US011766479B1

(12) United States Patent
Xiao et al.

(10) Patent No.: US 11,766,479 B1
(45) Date of Patent: *Sep. 26, 2023

(54) THERAPEUTIC USE OF ANTIBODIES AGAINST ENPP3

(71) Applicant: Zhejiang Shimai Pharmaceutical Co., Ltd., Zhejiang (CN)

(72) Inventors: Zuoxiang Xiao, Zhejiang (CN); Jiaping Peng, Zhejiang (CN); Dongwen Zhou, Zhejiang (CN); Wei Zhou, Zhejiang (CN)

(73) Assignee: Zhejiang Shimai Pharmaceutical Co., Ltd., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/815,367

(22) Filed: Jul. 27, 2022

Related U.S. Application Data

(63) Continuation of application No. PCT/CN2022/097597, filed on Jun. 8, 2022.

(51) Int. Cl.
*A61K 39/395* (2006.01)
*C07K 16/30* (2006.01)
*C07K 16/28* (2006.01)
*A61P 35/00* (2006.01)
*C07K 16/40* (2006.01)
*A61K 45/06* (2006.01)
*A61K 39/00* (2006.01)

(52) U.S. Cl.
CPC ........ *A61K 39/39558* (2013.01); *A61K 45/06* (2013.01); *A61P 35/00* (2018.01); *C07K 16/2809* (2013.01); *C07K 16/2896* (2013.01); *C07K 16/40* (2013.01); *A61K 2039/505* (2013.01); *C07K 2317/31* (2013.01); *C07K 2317/55* (2013.01); *C07K 2317/565* (2013.01); *C07K 2317/732* (2013.01); *C07K 2317/92* (2013.01)

(58) Field of Classification Search
CPC .......................... C07K 16/30; A61K 39/39558
See application file for complete search history.

(56) References Cited

U.S. PATENT DOCUMENTS

2011/0123550 A1* 5/2011 Shibayama ............. A61P 35/00
436/501

FOREIGN PATENT DOCUMENTS

WO WO-2005036176 A1 * 4/2005 ....... A61K 47/48407
WO WO 2005/061547 A2 7/2005
WO WO 2018/144784 A1 8/2018

OTHER PUBLICATIONS

Polyak et al. (Blood, vol. 99, No. 9, p. 3256-3262, 2002) (Year: 2002).*
Munodzana et al. (Infection and Immunity, vol. 66 No. 6, p. 2619-2624, 1998) (Year: 1998).*
Komenaka et al. (Clinics in Dermatology, 2004, vol. 22, p. 251-265) (Year: 2004).*
Evans et al. (Q. J. Med 1999: 92: 299-307) (Year: 1999).*
Cuzick et al. (The Lancet, vol. 361, p. 296-300, 2003) (Year: 2003).*
Hernandez-Ledesma (Peptides, vol. 30, p. 426-430, 2009) (Year: 2009).*
Paul (Fundamental Immunology, 3rd Edition, 1993, pp. 292-295) (Year: 1993).*
Schiffman et al. (The New England Journal of Medicine, Vo. 353, No. 20, p. 2101-2104, 2005) (Year: 2005).*
Bendig M. M. (Methods: A Companion to Methods in Enzymology, 1995; 8:83-93) (Year: 1995).*
Johnson and Wu (Methods in Molecular Biology, Antibody Engineering: Methods and Protocols, vol. 248, p. 11-25, 2004) (Year: 2004).*
Rudikoff et al. (Proc Natl Acad Sci USA 79: 1979-1983, 1982) (Year: 1982).*
Portolano (The Journal of Immunology, vol. 150, No. 3, p. 880-887, 1993) (Year: 1993).*
Beiboer (J. Mol. Biol. (2000) 296:833-849) (Year: 2000).*
Baeuerle et al., BiTE: A new class of antibodies that recruit T-cells. Drugs of the Future. Feb. 2008; 33(2): 137-147. DOI:10.1358/dof. 2008.033.02.1172578.
Bargou et al., Tumor regression in cancer patients by very low doses of a T cell-engaging antibody. Science. Aug. 15, 2008;321(5891):974-7. doi: 10.1126/science.1158545.

* cited by examiner

*Primary Examiner* — Michael Allen
(74) *Attorney, Agent, or Firm* — Wolf, Greenfield & Sacks, P.C.

(57) ABSTRACT

Disclosed herein are antibodies against ENPP3 and uses thereof, specifically monoclonal antibodies against ENPP3, bispecific antibodies against ENPP3 and CD3, nucleic acids including nucleotide sequences encoding the antibodies, vectors including the nucleic acids, and host cell including the nucleic acids or the vectors. Also disclosed are pharmaceutical compositions and conjugates including the antibodies, and therapeutic methods for using the antibodies.

20 Claims, 7 Drawing Sheets

Specification includes a Sequence Listing.

THERAPEUTIC USE OF ANTIBODIES AGAINST ENPP3

CROSS-REFERENCE TO RELATED APPLICATION

This application is a continuation of International Patent Application No. PCT/CN2022/097597, filed on Jun. 8, 2022. For all purposes under the law, the entire disclosure of the aforementioned application is incorporated by reference as part of the disclosure of this application.

REFERENCE TO AN ELECTRONIC SEQUENCE LISTING

The contents of the electronic sequence listing (L047370041US00-SUBSEQ-DFC.xml; Size: 46,779 bytes; and Date of Creation: Apr. 3, 2023) is herein incorporated by reference in its entirety.

FIELD OF THE INVENTION

The present invention is directed to antibodies against ENPP3, and uses of such antibodies, in particular their use in the treatment of cancers.

BACKGROUND OF THE INVENTION

Ectonucleotide pyrophosphatase/phosphodiesterase 3 (ENPP3, also known as CD203c), a 150 kDa protein, belongs to a series of ectoenzymes that hydrolyze extracellular pyrophosphate or phosphodiester bonds as well as intracellular nucleotides involved in glycosyltransferase activity. These ectoenzymes possess ATPase and ATP pyrophosphatase activities and are type II transmembrane proteins.

Previous studies indicated ENPP3 has functional relevance in multiple biological processes, for instance endometrial receptivity and embryo implantation. ENPP3 is upregulated in neoplastic mast cells in the context of mastocytosis, in acute basophilic leukemia, in neoplastic cells of the bile duct. More notably, ENPP3 has been found to play an important role in the development and invasion of tumors.

ENPP3 is expressed in multiple organs and cell types, including epithelial, mucosal surfaces, and notably basophils and mast cells. In contrast to the restricted expression in normal tissues, ENPP3 is highly expressed in renal cell carcinoma (RCC) and subsets of hepatocellular carcinoma (HCC). The expression pattern of ENPP3 shows the potential capability for tumor therapy.

SUMMARY OF THE INVENTION

The present disclosure provides novel antibodies targeting ENPP3 or antigen binding fragments thereof, which can be in a form of a monoclonal antibody or bispecific antibody, such as a bispecific T-cell engager (BiTE®). A variety of functional assays have demonstrated the potent anti-tumor effect of the antibodies.

In an aspect, the present disclosure provides an antibody specifically binding to ENPP3, or an antigen binding fragment thereof, comprising a light chain variable region (VL) and a heavy chain variable region (VH), wherein the VL comprises LCDRs 1-3 having the amino acid sequences as set forth in SEQ ID NOs: 1-3 respectively, and the VH comprises HCDRs 1-3 having the amino acid sequences as set forth in SEQ ID NOs: 6-8 respectively.

In some embodiments of the antibody or the antigen binding fragment thereof disclosed herein, the VL comprises an amino acid sequence having at least 80%, at least 85%, at least 90%, at least 95%, at least 98%, at least 99%, or 100% sequence identity to SEQ ID NO: 4, and the VH comprises an amino acid sequence having at least 80%, at least 85%, at least 90%, at least 95%, at least 98%, at least 99%, or 100% sequence identity to SEQ ID NO: 9. In some embodiments, the VL comprises an amino acid sequence as set forth in SEQ ID NO: 4 and the VH comprises an amino acid sequence as set forth in SEQ ID NO: 9.

In some embodiments, the antibody is of an isotype selected from the group consisting of IgG, IgA, IgM, IgE and IgD. In some embodiments, the antibody is of a subtype selected from the group consisting of IgG1, IgG2, IgG3, and IgG4.

In some embodiments, the antigen binding fragment can be selected from the group consisting of Fab, Fab', F(ab')$_2$, Fv, scFv, and ds-scFv.

In some embodiments, the antibody can be a monoclonal antibody. In some embodiments, the antibody comprises a light chain comprising an amino acid sequence having at least 80%, at least 85%, at least 90%, at least 95%, at least 98%, at least 99%, or 100% sequence identity to SEQ ID NO: 5 and a heavy chain comprising an amino acid sequence having at least 80%, at least 85%, at least 90%, at least 95%, at least 98%, at least 99%, or 100% sequence identity to SEQ ID NO: 10.

In other embodiments, the antibody can be a bispecific or a multi-specific antibody. In some embodiments, the antibody can be a bispecific antibody which further comprises a second antigen binding region binding to a second antigen. In some embodiments, the second antigen can be a tumor associated antigen or an immune cell antigen. In some embodiments, the second antigen can be a T-cell antigen. In some embodiments, the T-cell antigen can be selected from the group consisting of T cell receptor (TCR), CD3, CD4, CD8, CD16, CD25, CD28, CD38, CD44, CD62L, CD69, ICOS, 41-BB (CD137), and NKG2D.

In some embodiments, the second antigen is CD3, and the second antigen binding region comprises a VL and a VH, wherein the VL comprises LCDRs 1-3 having the amino acid sequences as set forth in SEQ ID NOs: 11-13 respectively, and the VH comprises HCDRs 1-3 having the amino acid sequences as set forth in SEQ ID NOs: 16-18 respectively.

In some embodiments, the second antigen binding region comprises a VL comprising an amino acid sequence having at least 80%, at least 85%, at least 90%, at least 95%, at least 98%, at least 99%, or 100% sequence identity to SEQ ID NO: 14 and a VH comprising an amino acid sequence having at least 80%, at least 85%, at least 90%, at least 95%, at least 98%, at least 99%, or 100% sequence identity to SEQ ID NO: 19. In some embodiments, the second antigen binding region comprises a VL comprising an amino acid sequence as set forth in SEQ ID NO: 14 and a VH comprising an amino acid sequence as set forth in SEQ ID NO: 19.

In some embodiments, the VL of the second antigen binding region is linked to the C-terminal of the VL of the antibody specifically binding to ENPP3, optionally via a first linker, and the VH of the second antigen binding region is linked to the C-terminal of the VH of the antibody specifically binding to ENPP3, optionally via a second linker, wherein the first linker and the second linker are the same or different.

In some embodiments, each of the first linker and the second linker independently comprises an amino acid selected from SEQ ID NO: 21 (GSGGGGSGGGGS) and SEQ ID NO: 22 (GSGGSGGGGSGGGGS). In some embodiments, the first linker comprises an amino acid sequence as set forth in SEQ ID NO: 21 (GSGGGGSGGGGS), and the second linker comprises an amino acid sequence as set forth in SEQ ID NO: 22 (GSGGSGGGGSGGGGS).

In some embodiments, the bispecific antibody comprises a light chain comprising an amino acid sequence having at least 80%, at least 85%, at least 90%, at least 95%, at least 98%, at least 99%, or 100% sequence identity to SEQ ID NO: 15 and a heavy chain comprising an amino acid sequence having at least 80%, at least 85%, at least 90%, at least 95%, at least 98%, at least 99%, or 100% sequence identity to SEQ ID NO: 20.

In some embodiments, the bispecific antibody is a bispecific T-cell engager (BITE®).

In another aspect, the present disclosure provides a bispecific antibody or an antigen binding fragment thereof, comprising a first antigen binding region binding to ENPP3 comprising a VL and a VH and a second antigen binding region binding to CD3 comprising a VL and a VH, wherein the VL of the first antigen binding region comprises LCDRs 1-3 having the amino acid sequences as set forth in SEQ ID NOs: 1-3 respectively, and the VH of the first antigen binding region comprises HCDRs 1-3 having the amino acid sequences as set forth in SEQ ID NOs: 6-8 respectively; and the VL of the second antigen binding region comprises LCDRs 1-3 having the amino acid sequences as set forth in SEQ ID NOs: 11-13 respectively, and the VH of the second antigen binding region comprises HCDRs 1-3 having the amino acid sequences as set forth in SEQ ID NOs: 16-18 respectively.

In some embodiments of the bispecific antibody or the antigen binding fragment thereof disclosed herein, the VL of the first antigen binding region comprises an amino acid sequence having at least 80%, at least 85%, at least 90%, at least 95%, at least 98%, at least 99%, or 100% sequence identity to SEQ ID NO: 4 and the VH of the first antigen binding region comprises an amino acid sequence having at least 80%, at least 85%, at least 90%, at least 95%, at least 98%, at least 99%, or 100% sequence identity to SEQ ID NO: 9; and the VL of the second antigen binding region comprises an amino acid sequence having at least 80%, at least 85%, at least 90%, at least 95%, at least 98%, at least 99%, or 100% sequence identity to SEQ ID NO: 14 and the VH of the second antigen binding region comprises an amino acid sequence having at least 80%, at least 85%, at least 90%, at least 95%, at least 98%, at least 99%, or 100% sequence identity to SEQ ID NO: 19.

In some embodiments, the VL of the first antigen binding region comprises an amino acid sequence as set forth in SEQ ID NO: 4 and the VH of the first antigen binding region comprises an amino acid sequence as set forth in SEQ ID NO: 9; and the VL of the second antigen binding region comprises an amino acid sequence as set forth in SEQ ID NO: 14 and the VH of the second antigen binding region comprises an amino acid sequence as set forth in SEQ ID NO: 19.

In some embodiments, the VL of the second antigen binding region is linked to the C-terminal of the VL of the first antigen binding region, optionally via a first linker, and the VH of the second antigen binding region is linked to the C-terminal of the VH of the first antigen binding region, optionally via a second linker, wherein the first linker and the second linker are the same or different.

In some embodiments, each of the first linker and the second linker independently comprises an amino acid selected from SEQ ID NO: 21 (GSGGGGSGGGGS) and SEQ ID NO: 22 (GSGGSGGGGSGGGGS). In some embodiments, the first linker comprises an amino acid sequence as set forth in SEQ ID NO: 21 (GSGGGGSGGGGS), and the second linker comprises an amino acid sequence as set forth in SEQ ID NO: 22 (GSGGSGGGGSGGGGS).

In some embodiments, the bispecific antibody comprises a light chain comprising an amino acid sequence having at least 80%, at least 85%, at least 90%, at least 95%, at least 98%, at least 99%, or 100% sequence identity to SEQ ID NO: 15 and a heavy chain comprising an amino acid sequence having at least 80%, at least 85%, at least 90%, at least 95%, at least 98%, at least 99%, or 100% sequence identity to SEQ ID NO: 20.

In some embodiments, the bispecific antibody can be a bispecific T-cell engager (BITE®).

In still another aspect, the present disclosure provides a nucleic acid comprising a nucleotide sequence encoding the antibody or the antigen binding fragment thereof disclosed herein or the bispecific antibody or the antigen binding fragment thereof disclosed herein.

In yet another aspect, the present disclosure provides a vector comprising the nucleic acid disclosed herein.

In another aspect, the present disclosure provides a host cell comprising the nucleic acid disclosed herein or the vector disclosed herein.

In still another aspect, the present disclosure provides a pharmaceutical composition comprising (i) the antibody or the antigen binding fragment thereof disclosed herein, or the bispecific antibody or the antigen binding fragment thereof disclosed herein, and (ii) a pharmaceutically acceptable carrier or excipient.

In some embodiments of the pharmaceutical composition disclosed herein, the pharmaceutical composition further comprising a second therapeutic agent. In some embodiments, the second therapeutic agent can be selected from an antibody, a chemotherapeutic agent and a small molecule drug. In some embodiments, the second therapeutic agent can be selected from a Bruton's tyrosine kinase (BTK) inhibitor, a PI3K inhibitor, a HDAC inhibitor, an ERK inhibitor, a MAPK inhibitor, a PD-1/PD-L1 inhibitor, a LAG3 inhibitor, a CTLA-4 inhibitor, a TIGIT inhibitor, a TIM3 inhibitor, and glucocorticoid.

In yet another aspect, the present disclosure provides a conjugate comprising the antibody or the antigen binding fragment thereof disclosed herein or the bispecific antibody or the antigen binding fragment thereof disclosed herein, and a chemical moiety conjugated thereto.

In some embodiments of the conjugate disclosed herein, the chemical moiety can be selected from the group consisting of a therapeutic agent, a detectable moiety, and an immune stimulatory molecule.

In another aspect, the present disclosure provides a method of treating a cancer in a subject comprising administering to the subject an effective amount of the antibody or the antigen binding fragment thereof disclosed herein, the bispecific antibody or the antigen binding fragment thereof disclosed herein, the pharmaceutical composition disclosed herein, or the conjugate disclosed herein.

In some embodiments of the method disclosed herein, the cancer is an ENPP3 positive cancer. In some embodiments, the cancer can be selected from the group consisting of mastocytosis, leukemia, kidney cancer, lung cancer, gastric cancer, ovarian cancer, breast cancer, pancreatic cancer, colon cancer, colorectal cancer, bile duct cancer, liver cancer, and Wilms tumor.

In some embodiments, the method further comprises administering to the subject a second therapeutic agent. In some embodiments, the second therapeutic agent can be selected from an antibody, a chemotherapeutic agent and a small molecule drug. In some embodiments, the second therapeutic agent can be selected from a Bruton's tyrosine kinase (BTK) inhibitor, a PI3K inhibitor, a HDAC inhibitor, an ERK inhibitor, a MAPK inhibitor, a PD-1/PD-L1 inhibitor, a LAG3 inhibitor, a CTLA-4 inhibitor, a TIGIT inhibitor, a TIM3 inhibitor, and glucocorticoid.

In another aspect, the present disclosure provides use of the antibody or the antigen binding fragment thereof disclosed herein, the bispecific antibody or the antigen binding fragment thereof disclosed herein, the pharmaceutical composition disclosed herein, or the conjugate disclosed herein in the manufacture of a medicament for treating a cancer in a subject. In some embodiments, the cancer is an ENPP3 positive cancer. In some embodiments, the cancer can be selected from the group consisting of mastocytosis, leukemia, kidney cancer, lung cancer, gastric cancer, ovarian cancer, breast cancer, pancreatic cancer, colon cancer, colorectal cancer, bile duct cancer, liver cancer, and Wilms tumor.

In still another aspect, the present disclosure provides the antibody or the antigen binding fragment thereof disclosed herein, the bispecific antibody or the antigen binding fragment thereof disclosed herein, the pharmaceutical composition disclosed herein, or the conjugate disclosed herein for use in treating a cancer in a subject. In some embodiments, the cancer is an ENPP3 positive cancer. In some embodiments, the cancer can be selected from the group consisting of mastocytosis, leukemia, kidney cancer, lung cancer, gastric cancer, ovarian cancer, breast cancer, pancreatic cancer, colon cancer, colorectal cancer, bile duct cancer, liver cancer, and Wilms tumor.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
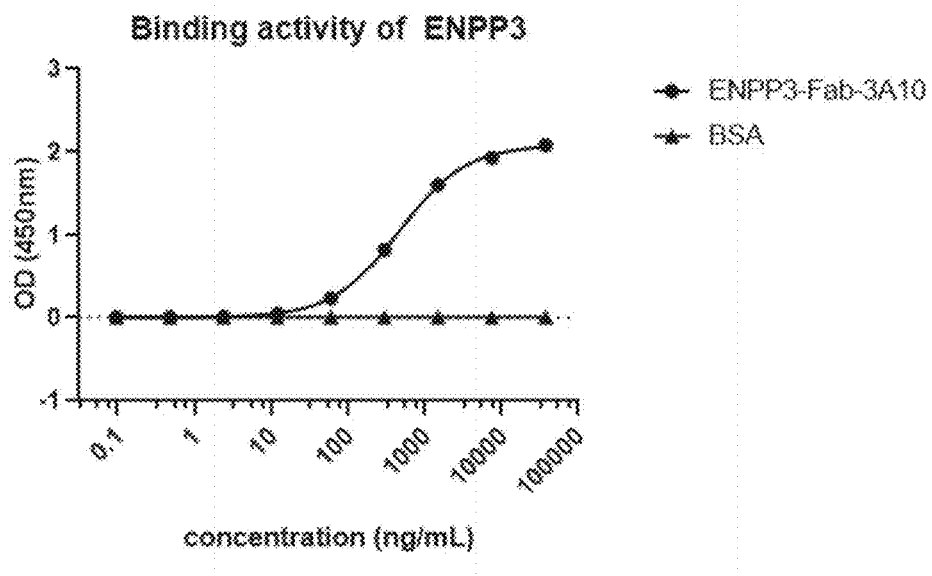
FIG. 1 shows binding of Fab 3A10 against recombinant human ENPP3 as measured by ELISA. BSA is used as negative control.

The aforementioned features and advantages of the invention as well as additional features and advantages thereof will be more clearly understood hereafter as a result of a detailed description of the following embodiments when taken in conjunction with the drawings.

The embodiments described herein with reference to drawings are explanatory, illustrative, and used to generally understand the present invention. The embodiments shall not be construed to limit the scope of the present invention. The same or similar elements and the elements having same or similar functions are denoted by like reference numerals throughout the descriptions.

Unless indicated or defined otherwise, all terms used have their usual meaning in the art, which will be clear to the skilled person. Reference is for example made to the standard handbooks, such as Leuenberger, H. G. W, Nagel, B. and Klbl, H. eds., "A multilingual glossary of biotechnological terms: (IUPAC Recommendations)", Helvetica Chimica Acta (1995), CH-4010 Basel, Switzerland; Sambrook et al, "Molecular Cloning: A Laboratory Manual" (2nd Ed.), Vols. 1-3, Cold Spring Harbor Laboratory Press (1989); F. Ausubel et al, eds., "Current protocols in molecular biology", Green Publishing and Wiley InterScience, New York (1987); Roitt et al., "Immunology (6th Ed.), Mosby/Elsevier, Edinburgh (2001); and Janeway et al., "Immunobiology" (6th Ed.), Garland Science Publishing/Churchill Livingstone, New York (2005), as well as the general background art cited above.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

Unless indicated or defined otherwise, the term "comprise", and variations such as "comprises" and "comprising", should be understood to imply the inclusion of a stated elements or step or group of elements or steps but not the exclusion of any other element or step or group of elements or steps.

As used herein, the term "antibody" refers to an immunoglobulin molecule which has the ability to specifically bind to a specific antigen. An antibody often comprises a variable region and a constant region in each of a heavy chain and a light chain. The variable regions of the heavy and light chains of antibodies contain a binding domain that interacts with an antigen. The constant regions of antibodies may mediate the binding of the immunoglobulin to host tissues or factors, including various cells of the immune system (such as effector cells) and components of the complement system such as C1q, the first component in the classical pathway of complement activation. Accordingly, most antibodies have a heavy chain variable region (VH) and a light chain variable region (VL) that together form the portion of the antibody that binds to the antigen.

A "light chain variable region" (VL) or "heavy chain variable region" (VH) consists of a "framework" region interrupted by three "complementarity determining regions" or "CDRs". The framework regions serve to align the CDRs for specific binding to an epitope of an antigen. The CDRs include the amino acid residues of an antibody that are primarily responsible for antigen binding. From aminoterminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as LCDR1, LCDR2, and LCDR3; CDRs 1, 2, and 3 of a VH domain are also referred to herein, respectively, as HCDR1, HCDR2, and HCDR3.

The assignment of amino acids to each VL and VH domain is in accordance with any conventional definition of CDRs. Conventional definitions include, the Kabat definition (Kabat, Sequences of Proteins of Immunological Interest (National Institutes of Health, Bethesda, Md., 1987 and 1991), the Chothia definition (Chothia & Lesk, J. Mol. Biol. 196:901-917, 1987; Chothia et al., Nature 342:878-883, 1989); a composite of Chothia Kabat CDR in which CDR-H1 is a composite of Chothia and Kabat CDRs; the AbM definition used by Oxford Molecular's antibody modelling software; and the CONTACT definition of Martin et al. (world wide web bioinfo.org.uk/abs). Kabat provides a widely used numbering convention (Kabat numbering system) in which corresponding residues between different heavy chains or between different light chains are assigned the same number. The present disclosure can use CDRs defined according to any of these numbering systems, although preferred embodiments use Kabat defined CDRs.

The term "antibody" as used herein should be understood in its broadest meaning, and includes monoclonal antibodies (including full-length monoclonal antibodies), polyclonal antibodies, antibody fragments, and multi-specific antibodies containing at least two different antigen binding regions (e.g., bispecific antibodies). The antibody may contain additional modifications, such as non-naturally occurring amino acids, mutations in Fc regions, and mutations in glycosylation sites. Antibodies also include post-translation modified antibodies, fusion proteins containing the antigenic determinants of the antibody, and immunoglobulin molecules containing any other modifications to antigen recognition sites, as long as these antibodies exhibit desired biological activity.

As used herein, the term "antigen binding fragment" of an antibody refers to one or more fragments of an antibody that retain the ability to specifically bind to an antigen (e.g., an ENPP3 protein). It has been shown that the antigen binding function of an antibody can be performed by fragments of a full-length antibody.

Examples of antigen binding fragments encompassed within the term "antigen binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fab' fragment, which is essentially an Fab with part of the hinge region(see, FUNDAMENTAL IMMUNOLOGY (Paul ed., 3.sup.rd ed. 1993); (iv) a Fd fragment consisting of the VH and CH1 domains; (v) a Fd' fragment having VH and CH1 domains and one or more cysteine residues at the C-terminus of the CH1 domain; (vi) a Fv fragment consisting of the VL and VH domains of a single arm of an antibody, (vii) a dAb fragment (Ward et al., (1989) Nature 341:544-546), which consists of a VH domain; (viii) an isolated complementarity determining region (CDR); and (ix) a nanobody, a heavy chain variable region containing a single variable domain and two constant domains. Furthermore, although the two domains of the Fv fragment, VL and VH are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding fragment" of an antibody. Furthermore, the term also includes a "linear antibody" comprising a pair of tandem Fd segments (VH-CH1-VH-CH1), which forms an antigen binding region together with a complementary light chain polypeptide, and a modified version of any of the foregoing fragments, which retains antigen binding activity.

These antigen binding fragments can be obtained using conventional techniques known to those with skill in the art, and the fragments are screened for utility in the same manner as are intact antibodies.

As used herein, the term "binding" or "specifically binding" refers to a non-random binding reaction between two molecules, such as between an antibody and its target antigen. The binding specificity of an antibody can be determined based on affinity and/or avidity. The affinity, represented by the equilibrium constant for the dissociation of an antigen with an antibody (KD), is a measure for the binding strength between an antigenic determinant and an antigen-binding site on the antibody: the lesser the value of the KD, the stronger the binding strength between an antigenic determinant and the antibody. Alternatively, the affinity can also be expressed as the affinity constant (KA), which is 1/KD.

Avidity is the measure of the strength of binding between an antibody and the pertinent antigen. Avidity is related to both the affinity between an antigenic determinant and its antigen binding site on the antibody and the number of pertinent binding sites present on the antibody. Typically, an antibody will bind to an antigen with a dissociation constant (KD) of $10^{-5}$ to $10^{-12}$ M or less, and preferably $10^{-7}$ to $10^{-12}$ M or less and more preferably $10^{-8}$ to $10^{-12}$ M, and/or with a binding affinity of at least $10^7$ $M^{-1}$, preferably at least 108 $M^{-1}$, more preferably at least 109 $M^{-1}$, such as at least 1012 $M^{-1}$. Any KD value greater than $10^{-4}$ M is generally considered to indicate non-specific binding. Specifically binding of an antibody to an antigen or antigenic determinant can be determined in any suitable manner known, including, for example, Scatchard analysis and/or competitive binding assays, such as radioimmunoassays (RIA), enzyme immunoassays (EIA) and sandwich competition assays, and the different variants thereof known in the art.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. The epitope defines the smallest binding site of an antibody and therefore is the specific target of the antibody or antigen binding fragment thereof.

As used herein, the term "sequence identity" refers to the extent to which two sequences (amino acid) have the same residue at the same positions in an alignment. For example, "an amino acid sequence is X % identical to SEQ ID NO: Y" refers to % identity of the amino acid sequence to SEQ ID NO:Y and is elaborated as X % of residues in the amino acid sequence are identical to the residues of sequence disclosed in SEQ ID NO: Y.

Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-2 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, He, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Nat. Acad Sci. USA 81: 140-144, 1984; Kyte & Doolittle, J Mol. Biol. 157: 105-132, 198 1, and Goldman et al., Ann. Rev. Biophys. Chem. 15: 321-353, 1986, all incorporated herein in their entirety by reference.

As used herein, the term "monoclonal antibody" refers to an antibody obtained from a substantially homogeneous antibody population. That is, each antibodies constituting the population are the same, except for possible naturally occurring mutations in small amount. Monoclonal antibodies are highly specific and are directed against a single antigen. The term "monoclonal antibody" herein is not limited to antibodies produced by hybridoma technology, and should not be interpreted as requiring production of antibodies by any specific method.

The term "bispecific antibody" is in the context of the present invention to be understood as an antibody having two different antigen-binding regions defined by different antibody sequences. This can be understood as different target binding but includes as well binding to different epitopes in one target.

As used herein, the term "tumor associated antigen" refers to an antigen that is differentially expressed in cancer cells compared to normal cells, and therefore can be used to target cancer cells.

As used herein, the term "CD3" refers to the human CD3 protein complex, which has five peptide chains, γ chain, δ chain, ε chain, ζ chain and η chain, and is associated with the T cell receptor α and β chains to form a TCR-CD3 complex. The term includes any CD3 variants, isoforms and species homologs which are naturally expressed by cells, including T cells, or are expressed on cells transfected with genes or cDNA encoding the aforementioned chains.

As used herein, the term "bispecific T-cell engager" or "BiTE®" refers to a polypeptide chain molecule having two antigen-binding domains, one of which binds to a T-cell antigen and the second of which binds to an antigen present on the surface of target cells (See, PCT Publication WO 05/061547; Baeuerle et al., 2008, Drugs of the Future 33: 137-147; Bargou, et al., 2008, Science 321:974-977, which are incorporated herein by reference in their entireties). Thus, the BiTE® of the disclosure has an antigen binding region that binds to ENPP3 and a second antigen binding region that is directed towards a T-cell antigen.

As used herein, the term "vector" is intended to refer to a nucleic acid molecule capable of transporting another nucleic acid to which it has been linked.

As used herein, the term "host cell" refers to a cell into which an expression vector has been introduced.

The term "pharmaceutically acceptable" means that the carrier or adjuvant is compatible with the other ingredients of the composition and not substantially deleterious to the recipient thereof and/or that such carrier or adjuvant is approved or approvable for inclusion in a pharmaceutical composition for parenteral administration to humans.

As used herein, the terms "treatment", "treating", "treat", and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment", as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease); (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the antibodies or compositions or conjugates disclosed herein to prevent or delay, to alleviate, or to arrest or inhibit development of the symptoms or conditions associated with diseases (e.g. cancers). The term "therapeutic effect" refers to the reduction, elimination, or prevention of the disease, symptoms of the disease, or side effects of the disease in the subject.

The term "effective amount" as used herein means the amount that, when administered to a subject for treating a disease, is sufficient to effect treatment for that disease.

The term "subject", as used herein, refers to any mammalian subject for whom diagnosis, treatment or therapy is desired. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc.

In an aspect, the present disclosure provides an antibody specifically binding to ENPP3, or an antigen binding fragment thereof, comprising a light chain variable region (VL) and a heavy chain variable region (VH), wherein the VL comprises LCDRs 1-3 having the amino acid sequences as set forth in SEQ ID NOs: 1-3 respectively, and the VH comprises HCDRs 1-3 having the amino acid sequences as set forth in SEQ ID NOs: 6-8 respectively.

In some embodiments, CDR sequences are defined according to Kabat numbering system.

When CDR sequences are defined according to Kabat numbering system, the VL of the antibody disclosed herein comprises LCDR1, LCDR2 and LCDR3 having the amino acid sequences as set forth in SEQ ID NO: 1 (SGSSS-NIGNNYVS), SEQ ID NO: 2 (DNNKRPS) and SEQ ID NO: 3 (GVWDSSLRAEL) respectively, and the VH of the antibody disclosed herein comprises HCDR1, HCDR2 and HCDR3 having the amino acid sequences as set forth in SEQ ID NO: 6 (NAWMS), SEQ ID NO: 7 (YISSSGSTIYY-ADSVKG) and SEQ ID NO: 8 (LAGPYYFDY) respectively.

In some embodiments of the antibody or the antigen binding fragment thereof disclosed herein, the VL comprises an amino acid sequence having at least 80%, at least 85%, at least 90%, at least 95%, at least 98%, at least 99%, or 100% sequence identity to SEQ ID NO: 4, and the VH comprises an amino acid sequence having at least 80%, at least 85%, at least 90%, at least 95%, at least 98%, at least 99%, or 100% sequence identity to SEQ ID NO: 9.

In some embodiments, the VL comprises a functional variant of the amino acid sequence as set forth in SEQ ID NO: 4 formed by insertion, deletion and/or substitution of one or more amino acid(s) therein, provided that the functional variant retains the ability of binding to ENPP3. In some embodiments, the VH comprises a functional variant of the amino acid sequence as set forth in SEQ ID NO: 9 formed by insertion, deletion and/or substitution of one or more amino acid(s) therein, provided that the functional variant retains the ability of binding to ENPP3.

The functional variant comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the amino acid sequence of the parent polypeptide. For example, the functional variant of SEQ ID NO: 4 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 4. For example, the functional variant of SEQ ID NO: 9 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 9.

In some embodiments, the functional variant of SEQ ID NO: 4 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 4 and formed by insertion, deletion and/or substitution of one or more amino acid(s) in SEQ ID NO: 4. In some embodiments, the functional variant of SEQ ID NO: 9 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 9 and formed by insertion, deletion and/or substitution of one or more amino acid(s) in SEQ ID NO: 9.

In the context of the functional variant, the number of the inserted, deleted and/or substituted amino acid is preferably no more than 40% of the total number of amino acids in the parent amino acid sequence, more preferably no more than 35%, more preferably 1-33%, and more preferably 5-30%, more preferably 10-25%, more preferably 15-20%. For example, the number of the inserted, deleted and/or substituted amino acid can be 1-20, preferably 1-10, more preferably 1-7, still more preferably 1-5, and most preferably 1-2. In a preferred embodiment, the number of the inserted, deleted and/or substituted amino acid is 1, 2, 3, 4, 5, 6, or 7.

In some embodiments, the insertion, deletion and/or substitution can be performed at framework (FR) regions, e.g., at FR1, FR2, FR3, and/or FR4.

In some embodiments, the substitution of one or more amino acid(s) can be conservative substitution of one or more amino acid(s). Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, He, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In a preferred embodiment, the VL comprises an amino acid sequence as set forth in SEQ ID NO: 4 and the VH comprises an amino acid sequence as set forth in SEQ ID NO: 9.

Based on the amino acid sequence of heavy chain constant regions of the antibody, a immunoglobulin molecule can be divided into five classes (isotypes): IgA, IgD, IgE, IgG, and IgM, and can be further divided into different subtypes, such as IgG1, IgG2, IgG3, IgG4, IgA1, IgA2, etc. The light chain of the antibody can be classified as a lambda (λ) chain or a kappa (κ) chain, based on the amino acid sequence of the light chain. The antibodies disclosed herein can be of any classes or subtypes above.

In some embodiments, the antibody can be of an isotype selected from the group consisting of IgG, IgA, IgM, IgE and IgD. In some embodiments, the antibody can be of a subtype selected from the group consisting of IgG1, IgG2, IgG3, and IgG4. In a preferred embodiment, the antibody is an IgG1 antibody.

The antibody disclosed herein can be an intact antibody or the antigen binding fragment thereof. The antigen binding fragment can be any fragments of the antibody that retain the ability to specifically bind to ENPP3. Examples of antigen binding fragments include but are not limited to a Fab fragment; a F(ab')$_2$ fragment; a Fab' fragment; a Fd fragment; a Fd' fragment; a Fv fragment; a scFv fragment; a dAb fragment; an isolated complementarity determining region (CDR); a nanobody; a linear antibody comprising a pair of tandem Fd segments (VH-CH1-VH-CH1), and a modified version of any of the foregoing fragments, which retains antigen binding activity.

In some embodiments, the antigen binding fragment can be selected from the group consisting of Fab, Fab', F(ab')$_2$, Fv, scFv, and ds-scFv. In a preferred embodiment, the antigen binding fragment is Fab or scFv. In another preferred embodiment, the antigen binding fragment is Fab.

In some embodiments, the antibody can be a monoclonal antibody. In some embodiments, the antibody comprises a light chain comprising an amino acid sequence having at least 80%, at least 85%, at least 90%, at least 95%, at least 98%, at least 99%, or 100% sequence identity to SEQ ID NO: 5 and a heavy chain comprising an amino acid sequence having at least 80%, at least 85%, at least 90%, at least 95%, at least 98%, at least 99%, or 100% sequence identity to SEQ ID NO: 10.

In some embodiments, the light chain comprises a functional variant of the amino acid sequence as set forth in SEQ ID NO: 5 formed by insertion, deletion and/or substitution of one or more amino acid(s) therein, provided that the functional variant retains the ability of binding to ENPP3. In some embodiments, the heavy chain comprises a functional variant of the amino acid sequence as set forth in SEQ ID NO: 10 formed by insertion, deletion and/or substitution of one or more amino acid(s) therein, provided that the functional variant retains the ability of binding to ENPP3.

For example, the functional variant of SEQ ID NO: 5 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 5. For example, the functional variant of SEQ ID NO: 10 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 10.

In some embodiments, the number of the inserted, deleted and/or substituted amino acid is preferably no more than 40% of the total number of amino acids in the parent amino acid sequence, more preferably no more than 35%, more preferably 1-33%, and more preferably 5-30%, more preferably $10^{-25}$%, more preferably 15-20%. For example, the number of the inserted, deleted and/or substituted amino acid can be 1-50, preferably 1-20, more preferably 1-10, still more preferably 1-5. In a preferred embodiment, the number of the inserted, deleted and/or substituted amino acid is 1, 2, 3, 4, 5, 6, or 7.

In some embodiments, the insertion, deletion and/or substitution can be performed at framework (FR) regions, e.g., at FR1, FR2, FR3 and/or FR4; and/or constant regions, e.g., CL, CH1, CH2 and/or CH3.

In some embodiments, the substitution of one or more amino acid(s) can be conservative substitution of one or more amino acid(s). Examples of conservative substitutions are as described above.

In a preferred embodiment, the light chain comprises an amino acid sequence as set forth in SEQ ID NO: 5 and the heavy chain comprises an amino acid sequence as set forth in SEQ ID NO: 10.

In other embodiments, the antibody can be a bispecific or a multi-specific antibody. In some embodiments, the antibody is a bispecific antibody which further comprises a second antigen binding region binding to a second antigen. In some embodiments, the second antigen can be a tumor associated antigen or an immune cell antigen.

Many tumor associated antigens associated with specific cancers have been identified in the art. In some embodiments, tumor-associated antigens are antigens that can potentially stimulate an obvious tumor-specific immune response. Some of these antigens are encoded by normal cells, but not necessarily expressed by normal cells. These antigens can be characterized as those that are usually silent (i.e., not expressed) in normal cells, those that are expressed only during certain stages of differentiation, and those that are expressed over time, such as embryonic and fetal antigens. Other cancer antigens are encoded by mutant cell genes such as oncogenes (e.g. activated ras oncogene), suppressor genes (e.g. mutant p53), and fusion proteins produced by internal deletions or chromosomal translocations. Other cancer antigens can be encoded by viral genes, such as those carried on RNA and DNA tumor viruses. Many other tumor associated antigens and antibodies against them are known and/or commercially available, and can also be produced by those skilled in the art.

Examples of tumor associated antigens include but are not limited to 5T4, alphafetoprotein, CA-125, carcinoembryonic antigen, CD19, CD20, CD22, CD23, CD30, CD33, CD40, CD56, CD79, CD78, CD123, CD138, c-Met, CSPG4, IgM, C-type lectin-like molecule 1 (CLL-1), EGFR, EGFRvIII, epithelial tumor antigen, ERBB2, FLT3, folate binding protein, GD2, GD3, HIV-1 envelope glycoprotein gp41, HIV-1 envelope glycoprotein gp120, melanoma-associated antigen, MUC-1, mutated p53, mutated ras, ROR1, GPC3, VEGFR2, and combinations thereof.

In some embodiments, the second antigen can be a T-cell antigen. In some embodiments, the T-cell antigen can be selected from the group consisting of T cell receptor (TCR), CD3, CD4, CD8, CD16, CD25, CD28, CD38, CD44, CD62L, CD69, ICOS, 41-BB (CD137), and NKG2D or any combination thereof. In some embodiments, the T-cell antigen is CD3, and the second antigen binding region binds to any of γ chain, δ chain, ε chain, ζ chain and η chain of CD3.

In some embodiments, the second antigen is CD3, and the second antigen binding region comprises a VL and a VH, wherein the VL comprises LCDRs 1-3 having the amino acid sequences as set forth in SEQ ID NOs: 11-13 respectively, and the VH comprises HCDRs 1-3 having the amino acid sequences as set forth in SEQ ID NOs: 16-18 respectively.

In some embodiments, CDR sequences are defined according to Kabat numbering system. When using Kabat defined CDR sequences, the VL of the second antigen binding region disclosed herein comprises LCDR1, LCDR2 and LCDR3 having the amino acid sequences as shown in SEQ ID NO: 11 (RSSTGAVTTSNYAN), SEQ ID NO: 12 (GANKRAP) and SEQ ID NO: 13 (ALWYSNLWV) respectively, and the VH of the second antigen binding region disclosed herein comprises HCDR1, HCDR2 and HCDR3 having the amino acid sequences as shown in SEQ ID NO: 16 (GFTFNTY), SEQ ID NO: 17 (RSKYNNYA) and SEQ ID NO: 18 (HGNFGSSYVSYFAY) respectively.

In some embodiments, the second antigen binding region comprises a VL comprising an amino acid sequence having at least 80%, at least 85%, at least 90%, at least 95%, at least 98%, at least 99%, or 100% sequence identity to SEQ ID NO: 14 and a VH comprising an amino acid sequence having at least 80%, at least 85%, at least 90%, at least 95%, at least 98%, at least 99%, or 100% sequence identity to SEQ ID NO: 19.

In some embodiments, the VL comprises a functional variant of the amino acid sequence as set forth in SEQ ID NO: 14 formed by insertion, deletion and/or substitution of one or more amino acid(s) therein, provided that the functional variant retains the ability of binding to CD3. In some embodiments, the VH comprises a functional variant of the amino acid sequence as set forth in SEQ ID NO: 19 formed by insertion, deletion and/or substitution of one or more amino acid(s) therein, provided that the functional variant retains the ability of binding to CD3.

For example, the functional variant of SEQ ID NO: 14 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 14. For example, the functional variant of SEQ ID NO: 19 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 19.

In some embodiments, the number of the inserted, deleted and/or substituted amino acid is preferably no more than 40% of the total number of amino acids in the parent amino acid sequence, more preferably no more than 35%, more preferably 1-33%, and more preferably 5-30%, more preferably $10^{-25}$%, more preferably 15-20%. For example, the number of the inserted, deleted and/or substituted amino acid can be 1-20, preferably 1-10, more preferably 1-7, still more preferably 1-5, and most preferably 1-2. In a preferred embodiment, the number of the inserted, deleted and/or substituted amino acid is 1, 2, 3, 4, 5, 6, or 7.

In some embodiments, the insertion, deletion and/or substitution can be performed at framework (FR) regions, e.g., at FR1, FR2, FR3, and/or FR4.

In some embodiments, the substitution of one or more amino acid(s) can be conservative substitution of one or more amino acid(s). Examples of conservative substitutions are as described above.

In a preferred embodiment, the second antigen binding region comprises a VL comprising an amino acid sequence as set forth in SEQ ID NO: 14 and a VH comprising an amino acid sequence as set forth in SEQ ID NO: 19.

In some embodiments, the VL of the second antigen binding region is linked to the C-terminal of the VL of the antibody specifically binding to ENPP3, optionally via a first linker, and the VH of the second antigen binding region is linked to the C-terminal of the VH of the antibody specifically binding to ENPP3, optionally via a second linker, wherein the first linker and the second linker are the same or different.

In some embodiments, each of the first linker and the second linker independently comprises an amino acid selected from SEQ ID NO: 21 (GSGGGGSGGGGS) and SEQ ID NO: 22 (GSGGSGGGGSGGGGS). In some embodiments, the first linker comprises an amino acid sequence as set forth in SEQ ID NO: 21 (GSGGGGSGGGGS), and the second linker comprises an amino acid sequence as set forth in SEQ ID NO: 22 (GSGGSGGGGSGGGGS).

In some embodiments, the bispecific antibody comprises a light chain comprising an amino acid sequence having at least 80%, at least 85%, at least 90%, at least 95%, at least 98%, at least 99%, or 100% sequence identity to SEQ ID NO: 15 and a heavy chain comprising an amino acid sequence having at least 80%, at least 85%, at least 90%, at least 95%, at least 98%, at least 99%, or 100% sequence identity to SEQ ID NO: 20.

In some embodiments, the light chain comprises a functional variant of the amino acid sequence as set forth in SEQ ID NO: 15 formed by insertion, deletion and/or substitution of one or more amino acid(s) therein, provided that the functional variant retains the ability of binding to ENPP3 and CD3. In some embodiments, the heavy chain comprises a functional variant of the amino acid sequence as set forth in SEQ ID NO: 20 formed by insertion, deletion and/or substitution of one or more amino acid(s) therein, provided that the functional variant retains the ability of binding to ENPP3 and CD3.

For example, the functional variant of SEQ ID NO: 15 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 15. For example, the functional variant of SEQ ID NO: 20 comprises or consists of an amino acid sequence having at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 20.

In some embodiments, the number of the inserted, deleted and/or substituted amino acid is preferably no more than 40% of the total number of amino acids in the parent amino acid sequence, more preferably no more than 35%, more preferably 1-33%, and more preferably 5-30%, more preferably $10^{-25}$%, more preferably 15-20%. For example, the number of the inserted, deleted and/or substituted amino acid can be 1-50, preferably 1-20, more preferably 1-10, still more preferably 1-5. In a preferred embodiment, the number of the inserted, deleted and/or substituted amino acid is 1, 2, 3, 4, 5, 6, or 7.

In some embodiments, the insertion, deletion and/or substitution can be performed at framework (FR) regions, e.g., at FR1, FR2, FR3 and/or FR4; and/or constant regions, e.g., CL, CH1, CH2 and/or CH3.

In some embodiments, the substitution of one or more amino acid(s) can be conservative substitution of one or more amino acid(s). Examples of conservative substitutions are as described above.

In a preferred embodiment, the light chain comprises an amino acid sequence as set forth in SEQ ID NO: 15 and the heavy chain comprises an amino acid sequence as set forth in SEQ ID NO: 20.

In some embodiments, the bispecific antibody can be a bispecific T-cell engager (BITE®). In some embodiments of the antibody or the antigen binding fragment thereof disclosed herein, the bispecific antibody is in form of an HBiTE as described in PCT application No. PCT/US2018/016524 (which is incorporated herein by reference in its entirety). In the HBiTE, the light chain, from N-terminus to C-terminus, comprises an anti-target VL domain, an anti-CD3 VL-CL and a monomeric human IgG1 Fc (e.g., mFc7.2); and the heavy chain, from N-terminus to C-terminus, comprises an anti-target VH domain, an anti-CD3 VH-CH1 and a monomeric human IgG1 Fc (e.g., mFc7.2). Monomeric Fc7.2 contains two amino acid mutations (T366L and Y407H) capable of inhibiting Fc homodimerization.

In another aspect, the present disclosure provides a bispecific antibody or an antigen binding fragment thereof, comprising a first antigen binding region binding to ENPP3 comprising a VL and a VH and a second antigen binding region binding to CD3 comprising a VL and a VH, wherein the VL of the first antigen binding region comprises LCDRs 1-3 having the amino acid sequences as set forth in SEQ ID NOs: 1-3 respectively, and the VH of the first antigen binding region comprises HCDRs 1-3 having the amino acid sequences as set forth in SEQ ID NOs: 6-8 respectively; and the VL of the second antigen binding region comprises LCDRs 1-3 having the amino acid sequences as set forth in SEQ ID NOs: 11-13 respectively, and the VH of the second antigen binding region comprises HCDRs 1-3 having the amino acid sequences as set forth in SEQ ID NOs: 16-18 respectively.

In some embodiments of the bispecific antibody or the antigen binding fragment thereof disclosed herein, the VL of the first antigen binding region comprises an amino acid sequence having at least 80%, at least 85%, at least 90%, at least 95%, at least 98%, at least 99%, or 100% sequence identity to SEQ ID NO: 4 and the VH of the first antigen binding region comprises an amino acid sequence having at least 80%, at least 85%, at least 90%, at least 95%, at least 98%, at least 99%, or 100% sequence identity to SEQ ID NO: 9; and the VL of the second antigen binding region comprises an amino acid sequence having at least 80%, at least 85%, at least 90%, at least 95%, at least 98%, at least 99%, or 100% sequence identity to SEQ ID NO: 14 and the VH of the second antigen binding region comprises an amino acid sequence having at least 80%, at least 85%, at least 90%, at least 95%, at least 98%, at least 99%, or 100% sequence identity to SEQ ID NO: 19.

In some embodiments, the VL of the first antigen binding region comprises a functional variant of the amino acid sequence as set forth in SEQ ID NO: 4 formed by insertion, deletion and/or substitution of one or more amino acid(s) therein, provided that the functional variant retains the ability of binding to ENPP3. In some embodiments, the VH of the first antigen binding region comprises a functional variant of the amino acid sequence as set forth in SEQ ID NO: 9 formed by insertion, deletion and/or substitution of one or more amino acid(s) therein, provided that the functional variant retains the ability of binding to ENPP3. In some embodiments, the VL of the second antigen binding region comprises a functional variant of the amino acid sequence as set forth in SEQ ID NO: 14 formed by insertion, deletion and/or substitution of one or more amino acid(s) therein, provided that the functional variant retains the ability of binding to CD3. In some embodiments, the VH of the second antigen binding region comprises a functional variant of the amino acid sequence as set forth in SEQ ID NO: 19 formed by insertion, deletion and/or substitution of one or more amino acid(s) therein, provided that the functional variant retains the ability of binding to CD3.

The functional variants of SEQ ID NOs: 4, 9, 14 and 19 can be those as described above.

In a preferred embodiment, the VL of the first antigen binding region comprises an amino acid sequence as set forth in SEQ ID NO: 4 and the VH of the first antigen binding region comprises an amino acid sequence as set forth in SEQ ID NO: 9; and the VL of the second antigen binding region comprises an amino acid sequence as set forth in SEQ ID NO: 14 and the VH of the second antigen binding region comprises an amino acid sequence as set forth in SEQ ID NO: 19.

In some embodiments, the VL of the second antigen binding region is linked to the C-terminal of the VL of the first antigen binding region, optionally via a first linker, and the VH of the second antigen binding region is linked to the C-terminal of the VH of the first antigen binding region, optionally via a second linker, wherein the first linker and the second linker are the same or different. In some embodiments, each of the first linker and the second linker independently comprises an amino acid selected from SEQ ID NO: 21 (GSGGGGSGGGGS) and SEQ ID NO: 22 (GSGGSGGGGSGGGGS). In some embodiments, the first linker comprises an amino acid sequence as set forth in SEQ ID NO: 21 (GSGGGGSGGGGS), and the second linker comprises an amino acid sequence as set forth in SEQ ID NO: 22 (GSGGSGGGGSGGGGS).

In some embodiments, the bispecific antibody comprises a single polypeptide chain comprising the first antigen binding region and the second antigen binding region, and optionally an Fc region.

The Fc region may be of any isotype, including, but not limited to, IgG1, IgG2, IgG3 and IgG4, and may comprise one or more mutations or modifications. In one embodiment, the Fc region is of IgG1 isotype or derived therefrom, optionally with one or more mutations or modifications. In one embodiment, the Fc region is human IgG1 Fc.

In one embodiment, the Fc region is effector-function-deficient. For example, the Fc region may be of an IgG1 isotype, or a non-IgG1 type, e.g. IgG2, IgG3 or IgG4, which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24):12161-12168 (2001).

In one embodiment, the Fc region comprises a mutation removing the acceptor site for Asn-linked glycosylation or is otherwise manipulated to change the glycosylation properties. For example, in an IgG1 Fc region, an N297Q mutation can be used to remove an Asn-linked glycosylation site. Accordingly, in a specific embodiment, Fc region comprises an IgG1 sequence with an N297Q mutation.

In a further embodiment, the Fc region is glyco-engineered to reduce fucose and thus enhance ADCC, e.g. by addition of compounds to the culture media during antibody production as described in US2009317869 or as described in van Berkel et al. (2010) Biotechnol. Bioeng. 105:350 or by using FUT8 knockout cells, e.g. as described in Yamane-Ohnuki et al. (2004) Biotechnol. Bioeng 87:614. ADCC may alternatively be optimized using the method described by Umaña et al. (1999) Nature Biotech 17:176. In a further embodiment, the Fc region has been engineered to enhance complement activation, e.g. as described in Natsume et al. (2009) Cancer Sci. 100:2411.

In some embodiments, the Fc region comprises modifications or mutations that can inhibit Fc homodimerization. In some embodiments, the Fc region comprises a variant of a human IgG1 Fc wildtype sequence. The variant can comprise amino acid substitutions at positions T366 and Y407 of human IgG1 (Kabat numbering). Preferably, T366 is substituted with L (Leucine). Preferably, Y407 is substituted with I(Isoleucine), F(Phenylalanine), L(Leucine), M(Methionine), H(Histidine), K(Lysine), S(Serine), Q(Glutamine), T(Threonine), W(Tryptophan), A(Alanine), G(Glycine) or N (Asparagine). More preferably, Y407 is substituted with H. In one embodiment, T366 is substituted with L, and Y407 is substituted with H.

In some embodiments, the Fc region can be a monomeric human IgG1 Fc (e.g., mFc7.2) as described in PCT application No. PCT/US2018/016524, which is incorporated herein by reference in its entirety.

In some embodiments, the bispecific antibody comprises a first polypeptide chain comprising the VL of the first antigen binding region and the VL of the second antigen binding region, and optionally an Fc region; and a second polypeptide chain comprising the VH of the first antigen binding region and the VH of the second antigen binding region, and optionally an Fc region. The Fc region can be those as describe above.

In some embodiments, the first polypeptide chain further comprises a light chain constant region (CL). In some embodiments, the first polypeptide chain comprises a monomeric human IgG1 Fc (e.g., mFc7.2) as described above. In some embodiments, the first polypeptide chain comprises, from N-terminal to C-terminal: the VL of the first antigen binding region, the VL of the second antigen binding region, CL and mFc7.2.

In some embodiments, the second polypeptide chain further comprises a heavy chain constant region (CH), e.g., CH1. In some embodiments, the first polypeptide chain comprises a monomeric human IgG1 Fc (e.g., mFc7.2) as described above. In some embodiments, the second polypeptide chain comprises, from N-terminal to C-terminal: the VH of the first antigen binding region, the VH of the second antigen binding region, CH1 and mFc7.2.

In some embodiments, the bispecific antibody comprises a light chain comprising an amino acid sequence having at least 80%, at least 85%, at least 90%, at least 95%, at least 98%, at least 99%, or 100% sequence identity to SEQ ID NO: 15 and a heavy chain comprising an amino acid sequence having at least 80%, at least 85%, at least 90%, at least 95%, at least 98%, at least 99%, or 100% sequence identity to SEQ ID NO: 20.

In some embodiments, the light chain comprises a functional variant of the amino acid sequence as set forth in SEQ ID NO: 15 formed by insertion, deletion and/or substitution of one or more amino acid(s) therein, provided that the functional variant retains the ability of binding to ENPP3 and CD3. In some embodiments, the heavy chain comprises a functional variant of the amino acid sequence as set forth in SEQ ID NO: 20 formed by insertion, deletion and/or substitution of one or more amino acid(s) therein, provided that the functional variant retains the ability of binding to ENPP3 and CD3.

The functional variants of SEQ ID NOs: 15 and 20 can be those as described above.

In a preferred embodiment, the light chain comprises an amino acid sequence as set forth in SEQ ID NO: 15 and the heavy chain comprises an amino acid sequence as set forth in SEQ ID NO: 20.

In some embodiments, the bispecific antibody can be a bispecific T-cell engager (BiTE®), preferably an HBiTE as described above.

In still another aspect, the present disclosure provides a nucleic acid comprising a nucleotide sequence encoding the antibody or the antigen binding fragment thereof disclosed herein or the bispecific antibody or the antigen binding fragment thereof disclosed herein.

In yet another aspect, the present disclosure provides a vector comprising the nucleic acid disclosed herein.

Any vector may be suitable for the present disclosure. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof. Suitable exemplary vectors include e.g., pBY, pGAR, pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

A recombinant expression vector may be any suitable recombinant expression vector. Suitable vectors comprise those designed for propagation and expansion or for expression or both, such as plasmids and viruses. For example, a vector may be selected from the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also may be used. Examples of plant expression vectors useful in the context of the disclosure comprise pBY, pBI01, pBI101.2, pBI101.3, pBI121 and pBIN19 (Clontech). Examples of animal expression vectors useful in the context of the disclosure comprise pcDNA, pEUK-Cl, pMAM, and pMAMneo (Clontech).

Recombinant expression vectors may be prepared using standard recombinant DNA techniques described in, for example, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Constructs of expression vectors, which are circular or linear, may be prepared to contain a replication system functional in a prokaryotic or eukaryotic host cell. Replication systems may be derived, e.g., from ColEl, 2µ plasmid, λ, SV40, bovine papilloma virus, and the like.

In another aspect, the present disclosure provides a host cell comprising the nucleic acid disclosed herein or the vector disclosed herein.

Any cell may be used as a host cell for the nucleic acids or the vectors of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, *Enterobactehaceae* such as *Escherichia*, e.g., *E. coli*; *Enterobacter*; *Erwinia*; *Klebsiella*; *Proteus*; *Salmonella*, e.g., *Salmonella typhimurium*, *Serratia*, e.g., *Serratia marcescans*, and *Shigella*; Bacilli such as *B. subtilis* and *B. licheniformis*; *Pseudomonas* such as *P. aeruginosa*; and *Streptomyces*. In some embodiments, the cell is a human cell. In some embodiments, the cell is an immune cell. In some embodiments, host cells include, for example, CHO cells, such as CHOS cells and CHO-K1 cells, or HEK293 cells, such as HEK293A, HEK293T and HEK293FS.

In still another aspect, the present disclosure provides a pharmaceutical composition comprising (i) the antibody or the antigen binding fragment thereof disclosed herein, or the bispecific antibody or the antigen binding fragment thereof disclosed herein; and (ii) a pharmaceutically acceptable carrier or excipient.

In some embodiments, the carrier or excipient for use with the composition disclosed herein includes but is not limited to maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In some embodiments of the pharmaceutical composition disclosed herein, the pharmaceutical composition further comprises a second therapeutic agent. In some embodiments, the second therapeutic agent can be selected from an antibody, a chemotherapeutic agent and a small molecule drug. In some embodiments, the second therapeutic agent can be selected from a Bruton's tyrosine kinase (BTK) inhibitor, a PI3K inhibitor, a HDAC inhibitor, an ERK inhibitor, a MAPK inhibitor, a PD-1/PD-L1 inhibitor, a LAGS inhibitor, a CTLA-4 inhibitor, a TIGIT inhibitor, a TIM3 inhibitor, and glucocorticoid, or any combination thereof.

In some embodiments, the therapeutic agent is a chemotherapeutic agent. The chemotherapeutic agents can include, for example, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, *vinca* alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors.

In yet another aspect, the present disclosure provides a conjugate comprising the antibody or the antigen binding fragment thereof disclosed herein or the bispecific antibody or the antigen binding fragment thereof disclosed herein, and a chemical moiety conjugated thereto.

In some embodiments of the conjugate disclosed herein, the chemical moiety is selected from the group consisting of a therapeutic agent, a detectable moiety, and an immune stimulatory molecule.

In some embodiments, the therapeutic agent includes but is not limited to immunomodulators, radioactive compounds, enzymes (for example perforin), chemotherapeutic agents (for example cis-platin), or a toxin. In some embodiments, the therapeutic agent can be such as maytansine, geldanamycin, tubulin inhibitors such as tubulin binding agents (e.g., auristatins), or minor groove binding agents such as calicheamicin.

Other suitable therapeutic agents include such as, small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin; peptide cytotoxins, i.e. proteins or fragments thereof with the ability to kill mammalian cells, for example, ricin, diphtheria toxin, *pseudomonas* bacterial exotoxin A, DNase and RNase; radio-nuclides, i.e. unstable isotopes of elements which decay with the concurrent emission of one or more of a α or β particles, or γ rays, for example, iodine-131, rhenium-186, indium-111, yttrium-90, bismuth-210, bismuth-213, actinium-225 and astatine-213; chelating agents may be used to facilitate the association of these radionuclides to the molecules, or multimers thereof.

In some embodiments, the detectable moiety can be selected from the group consisting of biotin, streptavidin, an enzyme or catalytically active fragment thereof, a radionuclide, a nanoparticle, a paramagnetic metal ion, or a fluorescent, phosphorescent, or chemiluminescent molecule. A detectable moiety for diagnostic purposes include for instance, fluorescent labels, radiolabels, enzymes, nucleic acid probes and contrast reagents.

In some embodiments, the immune stimulatory molecule is an immune effector molecules which stimulate immune response. For example, the immune stimulatory molecule can be cytokines such as IL-2 and IFN-γ, chemokines such as IL-8, platelet factor 4, melanoma growth stimulatory protein, complement activators; viral/bacterial protein domains, or viral/bacterial peptides.

In another aspect, the present disclosure provides a method of treating a cancer in a subject comprising administering to the subject an effective amount of the antibody or the antigen binding fragment thereof disclosed herein, the bispecific antibody or the antigen binding fragment thereof disclosed herein, the pharmaceutical composition disclosed herein, or the conjugate disclosed herein.

In some embodiments of the method disclosed herein, the cancer is an ENPP3 positive cancer. In some embodiments, the cancer can be selected from the group consisting of mastocytosis, leukemia, liver cancer, colon cancer, rectal cancer, colorectal cancer, bile duct cancer, Wilms tumor, pancreatic cancer, breast cancer, lung cancer, ovarian cancer, esophageal cancer, bladder cancer, prostate cancer, colorectal cancer, uterine cancer, cervical cancer, brain cancer, cervical cancer, gastric cancer, cholangiocarcinoma, chondrosarcoma, kidney cancer, thyroid cancer, skin cancer, glioma, neuroblastoma, lymphoma and myeloma. Preferably, the cancer is selected from the group consisting of mastocytosis, leukemia, kidney cancer (e.g. renal cell carcinoma), lung cancer, gastric cancer, ovarian cancer, breast cancer, pancreatic cancer, colon cancer, rectal cancer, colorectal cancer, bile duct cancer, liver cancer (e.g. hepatocellular carcinoma), and Wilms tumor.

In some embodiments, dosage administered to a subject may vary with the embodiment, the medicament employed, the method of administration, and the site and subject being treated. However, a dose should be sufficient to provide a therapeutic response. A clinician may determine the effective amount to be administered to a human or other subject in order to treat a medical condition. The precise amount required to be therapeutically effective may depend upon numerous factors, e.g., such as the activity of the antibody, and the route of administration.

A dose of the antibodies, compositions or conjugates described herein may be administered to a mammal at one time or in a series of sub-doses administered over a suitable period of time, e.g., on a daily, semi-weekly, weekly, bi-weekly, semi-monthly, bi-monthly, semi-annual, or annual basis, as needed. A dosage unit comprising an effective amount of antibodies, compositions or conjugates may be administered in a single daily dose, or the total daily dosage may be administered in two, three, four, or more divided doses administered daily, as needed.

A suitable means of administration may be selected by a medical practitioner. Route of administration may be parenteral, for example, administration by injection, transnasal administration, transpulmonary administration, or transcutaneous administration. Administration may be systemic or local by intravenous injection, intramuscular injection, intraperitoneal injection, subcutaneous injection. In some embodiments, the antibodies, compositions or conjugates are selected for parenteral delivery, for inhalation, or for delivery through the digestive tract, such as orally. Dose and method of administration may vary depending on the weight, age, condition, and the like of the subject, and may be suitably selected.

In some embodiments, the method further comprises administering to the subject a second therapeutic agent. In certain embodiments, the antibody, composition or conjugate disclosed herein is administered prior to, substantially simultaneously with, or after the administration of the second therapeutic agent.

In some embodiments, the second therapeutic agent is selected from an antibody, a chemotherapeutic agent and a small molecule drug. In some preferred embodiments, the second therapeutic agent can be selected from a Bruton's tyrosine kinase (BTK) inhibitor, a PI3K inhibitor, a HDAC inhibitor, an ERK inhibitor, a MAPK inhibitor, a PD-1/PD-L1 inhibitor, a LAGS inhibitor, a CTLA-4 inhibitor, a TIGIT inhibitor, a TIM3 inhibitor, and glucocorticoid, or any combination thereof.

In some embodiments, the second therapeutic agent is a chemotherapeutic agent. The chemotherapeutic agents can include, for example, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, *vinca* alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors.

In still another aspect, the present disclosure provides a method of detecting ENPP3 positive cancer in a subject comprising (i) contacting a sample obtained from the subject with the antibody or the antigen binding fragment thereof disclosed herein, the bispecific antibody or the antigen binding fragment thereof disclosed herein, or the conjugate disclosed herein; and (ii) detecting binding of the antibody or the antigen binding fragment thereof to ENPP3 in the sample.

In some embodiments, the antibody or the antigen binding fragment thereof is linked to a detectable moiety. The detectable moiety can be selected from the group consisting of biotin, streptavidin, an enzyme or catalytically active fragment thereof, a radionuclide, a nanoparticle, a paramagnetic metal ion, or a fluorescent, phosphorescent, or chemiluminescent molecule. A detectable moiety for diagnostic purposes include for instance, fluorescent labels, radiolabels, enzymes, nucleic acid probes and contrast reagents.

In some embodiments, the cancer is an ENPP3 positive cancer. Preferably, the cancer is selected from the group consisting of mastocytosis, leukemia, kidney cancer (e.g. renal cell carcinoma), lung cancer, gastric cancer, ovarian cancer, breast cancer, pancreatic cancer, colon cancer, rectal cancer, colorectal cancer, bile duct cancer, liver cancer (e.g. hepatocellular carcinoma), and Wilms tumor.

In yet another aspect, the present disclosure provides a pharmaceutical pack or kit comprising one or more containers filled with one or more of the ingredients of the pharmaceutical compositions described herein, such as the antibodies or the antigen binding fragment disclosed herein. Optionally, associated with such container(s) can be a notice in the form prescribed by a governmental agency regulating the manufacture, use or sale of pharmaceuticals or biological products, which notice reflects approval by the agency of manufacture, use or sale for human administration.

In a specific embodiment, the kit comprises a first container containing the antibodies or the antigen binding fragment disclosed herein. In a specific embodiment, the kit comprises a first container that is a vial containing the antibodies or the antigen binding fragment as a lyophilized sterile powder under vacuum, and the kit further comprises a second container comprising a pharmaceutically acceptable fluid.

In a specific embodiment, provided herein is an injection device containing the antibodies or the antigen binding fragment disclosed herein. In a specific embodiment, the injection device comprises the antibody in sterile solution. In a specific embodiment, the injection device is a syringe.

In still another aspect, the present disclosure provides a kit for detecting the presence of an ENPP3 antigen in a sample comprising the antibody or the antigen binding fragment thereof disclosed herein, the bispecific antibody or the antigen binding fragment thereof disclosed herein, or the conjugate disclosed herein. Preferably, the antibody or the antigen binding fragment thereof is linked to a detectable moiety. The detectable moiety can be selected from the group consisting of biotin, streptavidin, an enzyme or catalytically active fragment thereof, a radionuclide, a nanoparticle, a paramagnetic metal ion, or a fluorescent, phosphorescent, or chemiluminescent molecule. A detectable moiety for diagnostic purposes include for instance, fluorescent labels, radiolabels, enzymes, nucleic acid probes and contrast reagents.

In another aspect, the present disclosure provides use of the antibody or the antigen binding fragment thereof disclosed herein, the bispecific antibody or the antigen binding fragment thereof disclosed herein, the pharmaceutical composition disclosed herein, or the conjugate disclosed herein in the manufacture of a medicament for treating a cancer in a subject. In some embodiments, the cancer is an ENPP3 positive cancer.

In still another aspect, the present disclosure provides the antibody or the antigen binding fragment thereof disclosed herein, the bispecific antibody or the antigen binding fragment thereof disclosed herein, the pharmaceutical composition disclosed herein, or the conjugate disclosed herein for use in treating a cancer in a subject. In some embodiments, the cancer is an ENPP3 positive cancer.

In yet another aspect, the present disclosure provides use of the antibody or the antigen binding fragment thereof disclosed herein, the bispecific antibody or the antigen binding fragment thereof disclosed herein, or the conjugate disclosed herein in the manufacture of a kit for detecting ENPP3 positive cancer in a subject.

In still another aspect, the present disclosure provides the antibody or the antigen binding fragment thereof disclosed herein, the bispecific antibody or the antigen binding fragment thereof disclosed herein, or the conjugate disclosed herein for use in detecting ENPP3 positive cancer in a subject.

In some embodiments of the use disclosed herein, the ENPP3 positive cancer is preferably selected from the group consisting of mastocytosis, leukemia, kidney cancer (e.g. renal cell carcinoma), lung cancer, gastric cancer, ovarian cancer, breast cancer, pancreatic cancer, colon cancer, rectal cancer, colorectal cancer, bile duct cancer, liver cancer (e.g. hepatocellular carcinoma), and Wilms tumor.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Cell lines including HepG2 (human liver cancer cell line), LS174T (human colorectal cancer cell line) Jrukat (human lymphoma cell line) and SK-Nep-1 (human Wilms tumor cell line) were purchased from National Collection of Authenticated Cell Cultures.

A tumor cell line stably expressing ENPP3, LS174T-ENPP3, was generated by transient transfection of the commercial ENPP3 recombinant plasmid pCMV-human ENPP3 (Sino Biological) into LS174T cells using the agent Lipofectamine™ LTX Reagent with PLUS™ Reagent (Thermo) and transfection-specific media Opti-MEM™ I (Gibco). Cell culture was supplemented with hygromycin B and positive clones were selected. After 3-5 weeks, single positive clones were gradually separated and verified with flow-cytometry.

Human ENPP3 (CD203c) protein was purchased from ACROBiosystems. Anti-human IgG (γ-chain specific)-R-PE antibody, anti-human IgG (Fc-specific)-peroxidase antibody and monoclonal anti-Flag®M2-peroxidase were purchased from Sigma. M13KO7 helper phage was purchased from Invitrogen. Dynabeads™ Myone™ Streptavidin T1 was purchased from ThermoFisher Scientific. PE anti-His tag antibody was purchased from BioLegend.

Example 1. Panning and Screening of a Phage-Display Naive Human Fab Library for Identification of ENPP3 Antibodies Two large (size, 1011) phage-display naive human Fab libraries with peripheral blood B cells from about 30 healthy individuals were used for selection of antibodies against recombinant human ENPP3 conjugated to magnetic beads (Dynabeads™ Myone™ Streptavidin T1; ThermoFisher Scientific) as described previously (Zhu et al., J Virol 2006, 80:891-899) with minor modification that 5, 1, 0.2 and 0.2 mg of antigen was used in the first, second, third and fourth round of panning, respectively. After 4 rounds of biopanning, strong positive signals were observed by using polyclonal phage ELISA. The 4th round phage was subsequently subjected to test for specific binding to ENPP3. By soluble expression-based monoclonal enzyme-linked immunosorbent assay (SemELISA) and DNA sequencing analysis, a specific Fab clone, designated as 3A10, was identified. The Fab clone has a λ light chain.

The hexahistidine (HHHHHH, SEQ ID NO: 35)-tagged 3A10 Fab was expressed in *E. coli* strain HB2151 and purified from the soluble fraction of periplasm by using the Ni-NTA resin. Then ELISA was performed by using standard protocols to measure binding affinity to recombinant human ENPP3 (full-length extracellular domain). Briefly, the recombinant human ENPP3 (ACROBiosystems) was coated on Corning EIA/RIA high-binding 96-well plates (Corning Inc.) at 200 ng per well overnight at 4° C. and blocked with 3% nonfat milk in PBS (pH7.4). Five-fold serially diluted antibodies were added accordingly and then incubated at room temperature for 2 h. The plates were washed with PBS containing 0.05% TWEEN® 20. Bound antibodies were detected by HRP-conjugated anti-FLAG tag antibody (Sino Biological). The assay was developed at room temperature with TMB substrate (Solarbio) and OD value was measured at 450 nm with a microplate reader.

The result showed that Fab 3A10 has a binding affinity with $EC_{50}$ of 9.17 nM to human ENPP3 (FIG. 1), which is appropriate for therapeutic monoclonal antibody development and the construction of BiTE® type antibodies as well. In following examples, the Fab 3A10 sequence was used for the construction of monoclonal and bispecific antibodies.

Example 2. Construction and Characterization of Anti-ENPP3 Monoclonal Antibody

Fab clone 3A10 was used to construct an intact form of monoclonal antibody IgG1 against human ENPP3 (3A10 mAb). The heavy chain Fd fragment of 3A10 Fab was fused to the N-terminus of human IgG1 Fc fragment. Each of the light chain and heavy chain was constructed into the vector pBY separately. Construction and initial characterization of the 3A10 mAb were performed as follows.

Cloning of Anti-ENPP3 Monoclonal Antibody

To generate the construct of anti-ENPP3 monoclonal antibody, following primers were used:

pBY-SP-FP-Not1:

(SEQ ID NO: 23)
5'GAATGCGGCCGCAAACTACAAGACAGACTTGCAAAAGAAGGCATGCAC

AGCTCAGCACTGCTCTGTTG 3' (sense);

BI-ENPP3-3A10-VH-FP:

(SEQ ID NO: 24)
5'TCAGCACTGCTCTGTTGCCTGGTCCTCCTGACTGGGGTGAGGGCCGAG

GTGCAGCTGGTGGA 3' (sense);

ENPP3-3A10-Mab-VH-RP-OL:

(SEQ ID NO: 25)
5'CGGTGGGCATGTGTGAGTTTTGTCACAAGATTTGGGCT-
CAACTTTCT 3'

(antisense);

BI- ENPP3-3A10-VL-FP:

(SEQ ID NO: 26)
5'TCAGCACTGCTCTGTTGCCTGGTCCTCCTGACTGGGGTGAGGGCCCAG

TCTGTCGTGACGCAGC 3' (sense);

ENPP3-3A10-Mab-VL-RP-Xba1:

(SEQ ID NO: 27)
5'CGATTCTAGAATCATGAACATTCTGTAGGGGCCACTGTCTTC 3'
(antisense);

FC-FP-OL:

(SEQ ID NO: 28)
5'GACAAAACTCACACATGCCCACCG 3' (sense);

Fc-RP-Xba1:

(SEQ ID NO: 29)
5'CGATTCTAGAATCATTTACCCGGGGACAGGGAGAGGCT 3'
(antisense).

For the generation of light chain, the gene fragment of light chain was amplified from anti-ENPP3 Fab 3A10 with the primer pair BI-ENPP3-3A10-VL-FP/ENPP3-3A10-Mab-VL-RP-Xba1. A gene fragment encoding a leader peptide, which helps the expression of the target gene, was fused to the 5' end of the light chain PCR fragment by overlapping PCR by using the primer pair pBY-SP-FP-Not1/ENPP3-3A10-Mab-VL-RP-Xba1. The PCR product was cloned into a pBY vector by using restriction enzymes Not1/Xba1.

For the generation of heavy chain, the VH-CH1 gene fragment was amplified from anti-ENPP3 Fab 3A10 with the primer pair BI-ENPP3-3A10-VH-FP/ENPP3-3A10-Mab-VH-RP-OL. The PCR product was fused to the 3' end of a gene fragment of a signal peptide by overlapping PCR using the primer pair pBY-SP-FP-Not1/ENPP3-3A10-Mab-VH-RP-OL. The Fc domain was amplified from an irrelevant human IgG1 containing wild type Fc gene sequence with the primer pair FC-FP-OL/Fc-RP-Xba1. To obtain the full-length heavy chain, these two gene fragments were fused together by overlapping PCR using the primer pair pBY-SP-FP-Not1/Fc-RP-Xba1. The full-length heavy chain gene fragment was then cloned into the pBY plasmid via Not1 and Xba1 restriction sites.

Protein Expression, Purification and Initial Characterization

Anti-ENPP3 3A10 mAb was expressed in 293FS cells. The plasmids and transfection agent PEI were mixed at the ratio of 1:3 and then dropwise added into 293FS cell culture. The cells were continued to grow for 5-7 days after transfection. The cell culture was harvested by centrifugation at 8000 rpm for 20 min. The culture supernatant containing target proteins was loaded onto Gravity EshmunoA Column (Merck), and purified according to the manufacturer's instructions.

The purified proteins were subjected to SDS-PAGE. On a non-reducing SDS-PAGE, 3A10 mAb displays an apparent molecular weight (aMW) of approximately 150 kDa. On a reducing SDS-PAGE, the heavy chain and light chain have an apparent molecular weight of approximately 50 kDa and 25 kDa, respectively (data not shown).

The CDR sequences of 3A10 mAb according to the Kabat numbering system are shown in Table 1. The amino acid sequences of light chain variable region (VL) and heavy chain variable region (VH) of 3A10 mAb are shown in Table 2. The whole light chain and heavy chain sequences of 3A10 mAb are shown in Table 3.

TABLE 1

| CDR sequences of 3A10 mAb | | |
|---|---|---|
| LCDR1 | SGSSSNIGNNYVS | (SEQ ID NO: 1) |
| LCDR2 | DNNKRPS | (SEQ ID NO: 2) |
| LCDR3 | GVWDSSLRAEL | (SEQ ID NO: 3) |
| HCDR1 | NAWMS | (SEQ ID NO: 6) |
| HCDR2 | YISSSGSTIYYADSVKG | (SEQ ID NO: 7) |
| HCDR3 | LAGPYYFDY | (SEQ ID NO: 8) |

TABLE 2

| | VL and VH sequences of 3A10 mAb | |
|---|---|---|
| VL | QSVVTQPPSVSAAPGQKVTISCSGSSSNIGNNYVSWYQQL PGTAPKLLIYDNNKRPSGIPDRFSGSKSGTSATLGIDGLRT GDEAEYFCGVWDSSLRAELFAGGTKVTVL | SEQ ID NO: 4 |
| VH | EVQLVESGGGLVKPGGSLRLSCAASGFTFSNAWMSWVR QAPGKGLEWVSYISSSGSTIYYADSVKGRFTISRDNAKNS LYLQMNSLRAEDTAVYYCARLAGPYYFDYWGQGTLVTV SS | SEQ ID NO: 9 |

TABLE 3

| | Light chain and heavy chain sequences of 3A10 mAb | |
|---|---|---|
| Light chain | QSVVTQPPSVSAAPGQKVTISCSGSSSNIGNNYVSWYQQL PGTAPKLLIYDNNKRPSGIPDRFSGSKSGTSATLGIDGLRT GDEAEYFCGVWDSSLRAELFAGGTKVTVLSQPKAAPSVT LFPPSSEELQANKATLVCLISDFYPGAVTVAWKADSSPVK AGVETTTPSKQSNNKYAASSYLSLTPEQWKSHKSYSCQV THEGSTVEKTVAPTECS | SEQ ID NO: 5 |

TABLE 3-continued

Light chain and heavy chain sequences of 3A10 mAb

| | | |
|---|---|---|
| Heavy chain | EVQLVESGGGLVKPGGSLRLSCAASGFTFSNAWMSWVRQ<br>APGKGLEWVSYISSSGSTIYYADSVKGRFTISRDNAKNSLY<br>LQMNSLRAEDTAVYYCARLAGPYYFDYWGQGTLVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPELLGG<br>PSVFLFPPKPKDTLMISRTPEVTCVVVDVSHEDPEVKFNW<br>YVDGVEVHNAKTKPREEQYNSTYRVVSVLTVLHQDWLN<br>GKEYKCKVSNKALPAPIEKTISKAKGQPREPQVYTLPPSR<br>DELTKNQVSLTCLVKGFYPSDIAVEWESNGQPENNYKTTP<br>PVLDSDGSFFLYSKLTVDKSRWQQGNVFSCSVMHEALHN<br>HYTQKSLSLSPGK | SEQ ID NO: 10 |

Example 3. Binding of the Anti-ENPP3 Monoclonal Antibody to ENPP3

Figure 2:
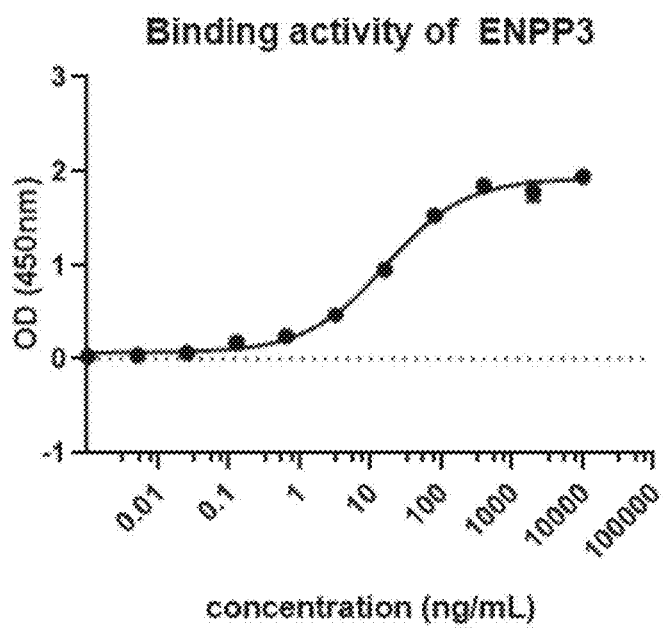
FIG. 2 shows binding of 3A10 mAb against recombinant human ENPP3 as measured by ELISA.

ELISA was performed according to standard protocols, to determine binding affinity of anti-ENPP3 3A10 mAb to recombinant human ENPP3 (AcroBiosystems). Briefly, recombinant human ENPP3 was coated on Corning EIA/RIA high-binding 96-well plates (Corning Inc.) at 100 ng per well overnight at 4° C. and blocked with 3% nonfat milk in PBS (pH7.4). Five-fold serially diluted antibodies were added and incubated at 37° C. for 1 h. The plates were washed with PBS containing 0.05% TWEEN® 20. Bound antibodies were detected by anti-human IgG (Fc-specific)-peroxidase antibody (Sigma). The assay was developed at room temperature with TMB substrate (Solarbio) and monitored at 450 nm with a microplate reader. The half-maximal binding ($EC_{50}$) was calculated by fitting the data to the Langmuir adsorption isotherm. The results are shown in FIG. 2.

The results indicate that 3A10 mAb binds to human ENPP3 with $EC_{50}$ of 107.2 pM, suggesting that 3A10 mAb has high binding affinity to human ENPP3.

Figure 3A:
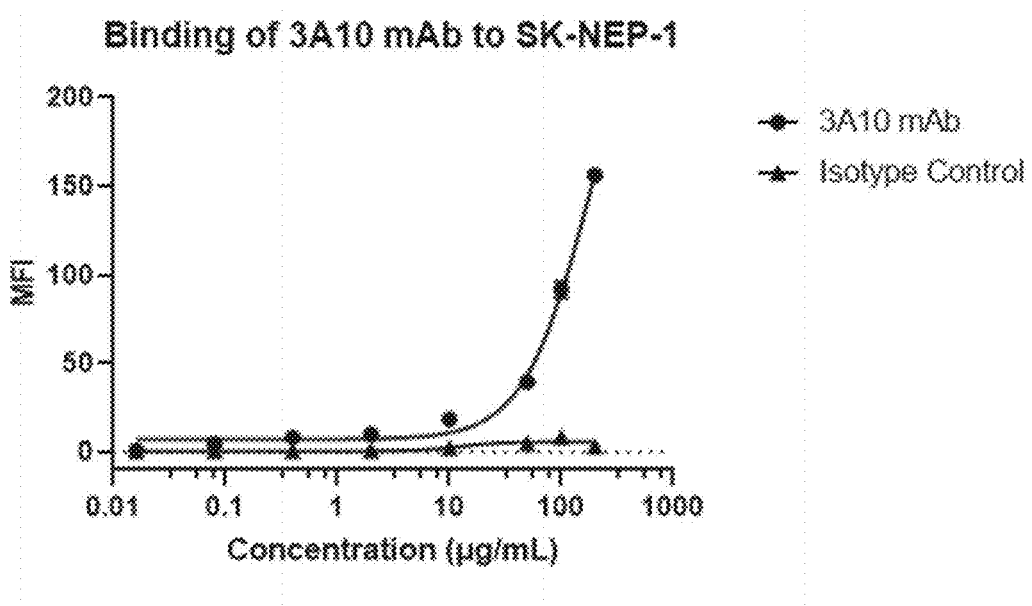
FIG. 3A shows binding of 3A10 mAb against ENPP3 positive cancer cell line SK-Nep-1 as measured by flow cytometry. An IgG4 isotype antibody is used as negative control.
Figure 3B:
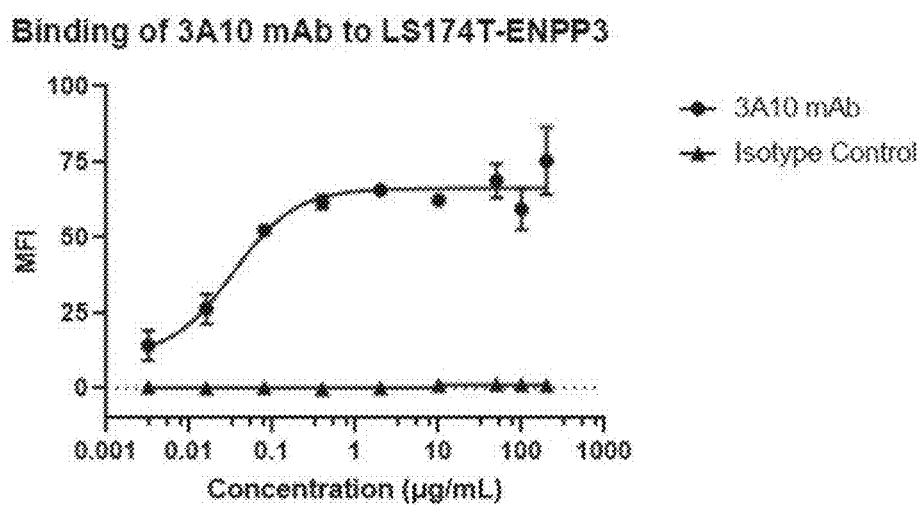
FIG. 3B shows binding of 3A10 mAb against LS174T-ENPP3 cells stably expressing ENPP3 as measured by flow cytometry. An IgG4 isotype antibody is used as negative control.

Example 4. Binding of the Anti-ENPP3 Monoclonal Antibody to Cancer Cell Lines To measure binding ability of the anti-ENPP3 3A10 mAb to cell surface-associated ENPP3, flow cytometry was carried out using ENPP3 positive cancer cell lines SK-Nep-1 and LS174T-ENPP3. About $5 \times 10^5$ cells were incubated with serial concentrations of antibodies on ice for 1 h, and an IgG4 isotype antibody was used as negative control. The cells were washed once with PBS containing 0.1% bovine serum albumin (PBSA) and resuspended in 100 µl PBSA. Then 1 µl anti-human IgG (Fc-specific)-FITC conjugate (Sigma) was added and incubated for 30 min. The cells were washed once with PBSA and then used for flow cytometry analysis. The half-maximal binding ($EC_{50}$) was calculated by fitting the data to the Langmuir adsorption isotherm. The results are shown in FIGS. 3A and 3B.

The results indicate that 3A10 mAb binds well to SK-Nep-1 and LS174T-ENPP3 cells, suggesting that 3A10 mAb have good binding ability to ENPP3 positive tumor cell lines.

Example 5. Anti-ENPP3 Monoclonal Antibody Mediated ADCC Killing Against Human Cancer Cell Line To evaluate ADCC killing of 3A10 mAb, HepG2 cells were used as target cells and NK cells were used as effector cells. Frozen NK cells were revived and cultured in RPMI1640 complete medium containing 20% FBS, 1% penicillin/streptomycin, and 50 IU of IL-2 in 5% $CO_2$ incubator at 37° C. overnight. Target cells HepG2 were prepared to a concentration of $1.5 \times 10^5$ cells/mL with the complete medium, and added to a 96-well plate at 100 µL/well, and incubated in a 37° C. incubator supplied with 5% $CO_2$ overnight. At the second day, a serial of concentration (200 µg/mL, 20 µg/mL, and 0 µg/mL) of 3A10 mAb were prepared with the complete medium, and an IgG4 isotype antibody was used as negative control. 100 µL of antibody solutions were added into the 96-well plate containing target cells. The NK cells were harvested and diluted to $3 \times 10^5$ cells/mL, and then added to the 96-well plate at 100 µL/well. The plate was incubated in 5% $CO_2$ incubator at 37° C. for 48 hours. The final concentrations of the antibody are 100 µg/mL, 10 µg/mL, and 0 µg/mL. After 48 h incubation, the culture media was removed and replaced with fresh complete medium containing 10% CCK8 at 100 µL/well, and the plate was incubated at 37° C. for 30 minutes. The OD value at 450 nm was measured with an ELISA reader. Killing efficiency was calculated according to the equation:

$$(OD_{Tumor+NK+0\mu g/mL\ mab} - OD_{Tumor+NK+x\mu g/mL\ mab}) / OD_{Tumor+NK+0\mu g/mL\ mab} \times 100\%,$$

in which x represents 10 or 100.

Figure 4:
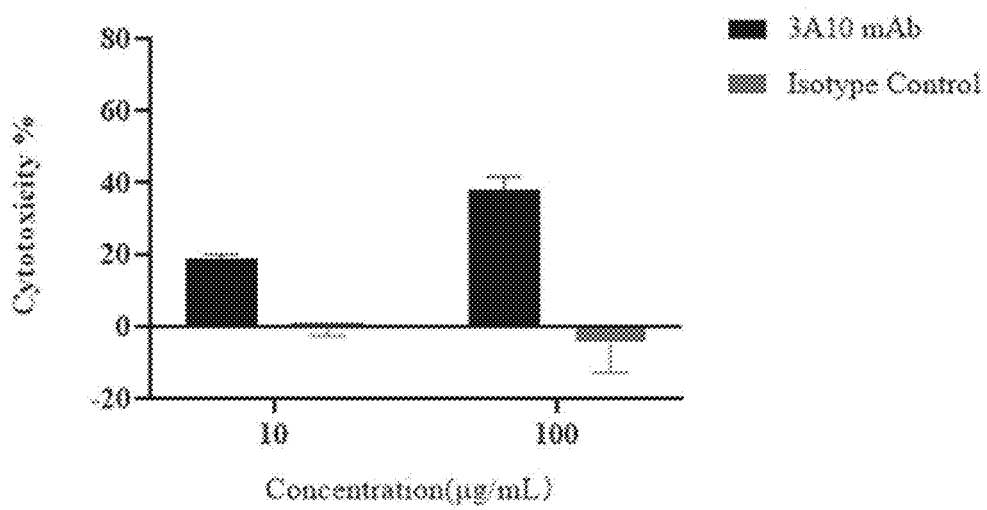
FIG. 4 shows ADCC killing of 3A10 mAb against HepG2 cells in the presence of NK cells. An IgG4 isotype antibody is used as negative control.

The results of ADCC killing of 3A10 mAb against HepG2 cells is shown in FIG. 4. The result shows that 3A10 mAb induces around 20% killing against tumor cells at 10 µg/mL, and over 36% killing against tumor cells at 100 µg/mL, while the control antibody IgG4 isotype does not induce any ADCC at the highest concentration of 100 µg/mL, suggesting that ADCC is triggered by specific binding of 3A10 mAb to ENPP3 positive tumor cells HepG2 and recruiting of NK cells through the Fc portion of the mAb. This demonstrates that 3A10 mAb possesses substantial capability of inducing ADCC killing against ENPP3 positive tumor cells.

Example 6. Construction and Characterization of Anti-ENPP3 Bispecific Antibody Bispecific T cell engager (BITE®) is a novel class of bispecific antibodies that can guide cytotoxic T cells to kill cancer cells by simultaneously binding to a tumor antigen and a T cell antigen, such as CD3 molecule on T cell surface. HBiTE as described in PCT application No. PCT/US2018/016524 (which is incorporated herein by reference in its entirety) is a specific form of BiTE®. HBiTE has a light chain and a heavy chain forming a heterodimer. The light chain, from N-terminus to C-terminus, comprises an anti-target (e.g. tumor antigen) VL domain, an anti-CD3 VL-CL and a monomeric human IgG1 Fc (e.g., mFc7.2). The heavy chain, from N-terminus to C-terminus, comprises an anti-target VH domain, an anti-CD3 VH-CH1 and a monomeric human IgG1 Fc (e.g., mFc7.2). Monomeric Fc7.2 contains two amino acid mutations (T366L and Y407H) capable of inhibiting Fc homodimerization. To generate ENPP3×CD3 HBiTE, the VL and VH domains of the above anti-ENPP3 antibody were fused to the N-terminus of VL and VH domains of anti-CD3 Fab via linkers GSGGGGSGGGGS (SEQ ID NO: 21) and GSGGSGGGGSGGGGS (SEQ ID NO: 22), respectively. The anti-CD3 Fab is further fused to the N terminus of mFc7.2. The light chain and heavy chain were constructed into a single vector pBY respectively for expression in mammalian cells. Construction and initial characterization of the bispecific antibody targeting ENPP3 and CD3 (3A10-based ENPP3×CD3 HBiTE) were performed as follows.

Cloning of the Bispecific Antibody Targeting ENPP3 and CD3

To generate construct of the bispecific antibody 3A10-based ENPP3×CD3 HBiTE, following primers were used:

```
pBY-SP-FP-Not1:
                                      (SEQ ID NO: 23)
5'GAATGCGGCCGCAAACTACAAGACAGACTTGCAAAAGAAGGCATGCA

CAGCTCAGCACTGCTCTGTTG 3' (sense);

BI-ENPP3-3A10-VH-FP:
                                      (SEQ ID NO: 24)
5'TCAGCACTGCTCTGTTGCCTGGTCCTCCTGACTGGGGTGAGGGCCGA

GGTGCAGCTGGTGGA 3' (sense);

BI- ENPP3-3A10-VH-RP:
                                      (SEQ ID NO: 30)
5'ACCTCCGCCTGAACCCCCGGATCCTGAGGAGACGGTGACCAGGGTT

3' (antisense);

BI- ENPP3-3A10-VL-FP:
                                      (SEQ ID NO: 26)
5'TCAGCACTGCTCTGTTGCCTGGTCCTCCTGACTGGGGTGAGGGCCCA

GTCTGTCGTGACGCAGC 3' (sense);

BI- ENPP3-3A10-VL-RP:
                                      (SEQ ID NO: 31)
5'GCCAGAGCCACCTCCGCCGGATCCTAGGACGGTCACCTTGGTCCCT

3' (antisense);

CD3FC-VH-FP-BamH1:
                                      (SEQ ID NO: 32)
5'GGATCCGGGGGTTCAGGCGGAGGTGGCTCTGG 3' (sense);

CD3FC-VL-FP:
                                      (SEQ ID NO: 33)
5' GGATCCGGCGGAGGTGGCTCTGGC 3' (sense);

FC-RP-Xba1-DelK:
                                      (SEQ ID NO: 34)
5' TGATCTAGAATTAACCCGGAGACAGGGAGAGGCTCT 3'
(antisense).
```

For the generation of the bispecific antibody, the gene fragments of VH and VL domains were amplified from 3A10 Fab with primer pairs BI-ENPP3-3A10-VH-FP/BI-ENPP3-3A10-VH-RP and BI-ENPP3-3A10-VL-FP/BI-ENPP3-3A10-VL-RP, respectively. The PCR products were fused to the 3' end of a signal peptide by overlapping PCR using the primer pairs pBY-SP-FP-Not 1/BI-ENPP3-3A10-VH-RP and pBY-SP-FP-Nott/BI-ENPP3-3A10-VL-RP, respectively. The fragments of an anti-CD3 hSP34 VL-CL and VH-CH1 and a complete Fc were amplified from the pBY vector containing the fragments of the CD3 bispecific antibody based on the same HBiTE format, with primer pairs CD3FC-VL-FP/FC-RP-Xba1-DelK and CD3FC-VH-FP-BamH1/FC-RP-Xba1-DelK, respectively. To obtain the full-length light chain and heavy chain, ENPP3 VL/VH fragments containing signal peptide and CD3 VL-CL-Fc/CD3 VH-CH1-Fc were fused by overlapping using primer pairs pBY-SP-FP-Not1/Fc-RP-XabI-DelK. The full-length light and heavy chain gene fragment were then cloned into two pBY plasmids via the Not1 and Xba1 restriction sites. The 3A10-based ENPP3×CD3 HBiTE was designated as CMD016.

Protein Expression, Purification and Initial Characterization

CMD016 was expressed in 293FS. The plasmids and transfection agent PEI were mixed at ratio 1:3 and then added into 293FS cell culture. The cells were continued to grow for 5-7 days after transfection. The cell culture was harvested by centrifugation at 8000 rpm for 20 min. The culture supernatant containing target proteins were loaded onto Gravity EshmunoA Column (Merck), and purified according to the manufacturer's instructions.

The purified proteins were subjected to SDS-PAGE. On a non-reducing SDS-PAGE, CMD016 displays an apparent molecular weight (aMW) of approximately 120 kDa. On a reducing SDS-PAGE, the heavy chain and light chain are close to each other with an apparent molecular weight of approximately 62 kDa (data not shown). The CDR sequences of CMD016 according to the Kabat numbering system are shown in Table 4. The amino acid sequences of light chain variable region (VL) and heavy chain variable region (VH) of CMD016 are shown in Table 5. The whole light chain and heavy chain sequences of CMD016 are shown in Table 6.

TABLE 4

| CDR sequences of CMD016 | | |
|---|---|---|
| LCDR1 against ENPP3 | SGSSSNIGNNYVS | (SEQ ID NO: 1) |
| LCDR2 against ENPP3 | DNNKRPS | (SEQ ID NO: 2) |
| LCDR3 against ENPP3 | GVWDSSLRAEL | (SEQ ID NO: 3) |
| HCDR1 against ENPP3 | NAWMS | (SEQ ID NO: 6) |
| HCDR2 against ENPP3 | YISSSGSTIYYADSVKG | (SEQ ID NO: 7) |
| HCDR3 against ENPP3 | LAGPYYFDY | (SEQ ID NO: 8) |
| LCDR1 against CD3 | RSSTGAVTTSNYAN | (SEQ ID NO: 11) |
| LCDR2 against CD3 | GANKRAP | (SEQ ID NO: 12) |
| LCDR3 against CD3 | ALWYSNLWV | (SEQ ID NO: 13) |
| HCDR1 against CD3 | GFTFNTY | (SEQ ID NO: 16) |
| HCDR2 against CD3 | RSKYNNYA | (SEQ ID NO: 17) |
| HCDR3 against CD3 | HGNFGSSYVSYFAY | (SEQ ID NO: 18) |

TABLE 5

VL and VH sequences of CMD016

| | | |
|---|---|---|
| VL against ENPP3 | QSVVTQPPSVSAAPGQKVTISCSGSSSNIGNNYVSWY QQLPGTAPKLLIYDNNKRPSGIPDRFSGSKSGTSATLGI DGLRTGDEAEYFCGVWDSSLRAELFAGGTKVTVL | SEQ ID NO: 4 |
| VL against CD3 | EIVVTQSPATLSVSPGERATLSCRSSTGAVTTSNYAN WVQQKPGQAPRGLIGGANKRAPGVPARFSGSLSGDE ATLTISSLQSEDFAVYYCALWYSNLWVFGQGTKLEIK | SEQ ID NO: 14 |
| VH against ENPP3 | EVQLVESGGGLVKPGGSLRLSCAASGFTFSNAWMSW VRQAPGKGLEWVSYISSSGSTIYYADSVKGRFTISRDN AKNSLYLQMNSLRAEDTAVYYCARLAGPYYFDYWG QGTLVTVSS | SEQ ID NO: 9 |
| VH against CD3 | EVQLVESGGGLVQPGGSLRLSCAASGFTFNTYAMNW VRQAPGKGLEWVARIRSKYNNYATYYADSVKGRFTI SRDDSKNTLYLQMNSLRAEDTAVYYCARHGNFGSSY VSYFAYWGQGTTVTVSS | SEQ ID NO: 19 |

TABLE 6

Light chain and heavy chain sequences of CMD016

| | | |
|---|---|---|
| Light chain | QSVVTQPPSVSAAPGQKVTISCSGSSSNIGNNYVSWY QQLPGTAPKLLIYDNNKRPSGIPDRFSGSKSGTSATL GIDGLRTGDEAEYFCGVWDSSLRAELFAGGTKVTVL GSGGGGSGGGGSEIVVTQSPATLSVSPGERATLSCRS STGAVTTSNYANWVQQKPGQAPRGLIGGANKRAPG VPARFSGSLSGDEATLTISSLQSEDFAVYYCALWYSN LWVFGQGTKLEIKRTVAAPSVFIFPPSDEQLKSGTAS VVCLLNNFYPREAKVQWKVDNALQSGNSQESVTEQ DSKDSTYSLSSTLTLSKADYEKHKVYACEVTHQGLS SPVTKSFNRGECPPCPAPELLGGPSVFLFPPKPKDTL MISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSRDEL TKNQVSLLCLVKGFYPSDIAVEWESNGQPENNYKTT PPVLDSDGSFFLHSKLTVDKSRWQQGNVFSCSVMHE ALHNHYTQKSLSLSPG | SEQ ID NO: 15 |
| Heavy chain | EVQLVESGGGLVKPGGSLRLSCAASGFTFSNAWMS WVRQAPGKGLEWVSYISSSGSTIYYADSVKGRFTISR DNAKNSLYLQMNSLRAEDTAVYYCARLAGPYYFD YWGQGTLVTVSSGSGGSGGGGSGGGGSEVQLVESG GGLVQPGGSLRLSCAASGFTFNTYAMNWVRQAPGK GLEWVARIRSKYNNYATYYADSVKGRFTISRDDSK NTLYLQMNSLRAEDTAVYYCARHGNFGSSYVSYFA YWGQGTTVTVSSASTKGPSVFPLAPSSKSTSGGTAA LGCLVKDYFPEPVTVSWNSGALTSGVHTFPAVLQSS GLYSLSSVVTVPSSSLGTQTYICNVNHKPSNTKVDK KVEPKSCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELTKNQ VSLLCLVKGFYPSDIAVEWESNGQPENNYKTTPPVL DSDGSFFLHSKLTVDKSRWQQGNVFSCSVMHEALH NHYTQKSLSLSPG | SEQ ID NO: 20 |

Example 7. Binding of the Bispecific Antibody to ENPP3 and CD3

Figure 5A:
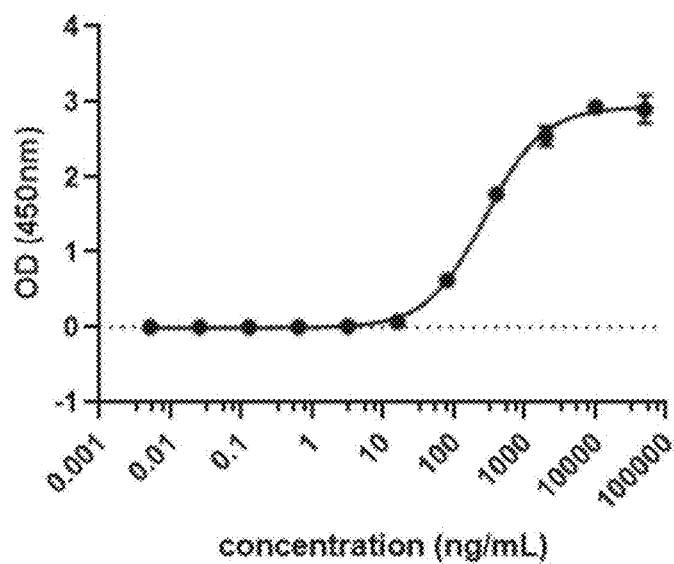
FIG. 5A shows binding of CMD016 against recombinant human ENPP3 as measured by ELISA.

To determine binding affinity of the bispecific antibody CMD016 to both ENPP3 and CD3, ELISA experiments were performed as described in Example 3, with the coating proteins of human ENPP3 or human CD3. The results are shown in FIGS. 5A-5B.

Figure 5B:
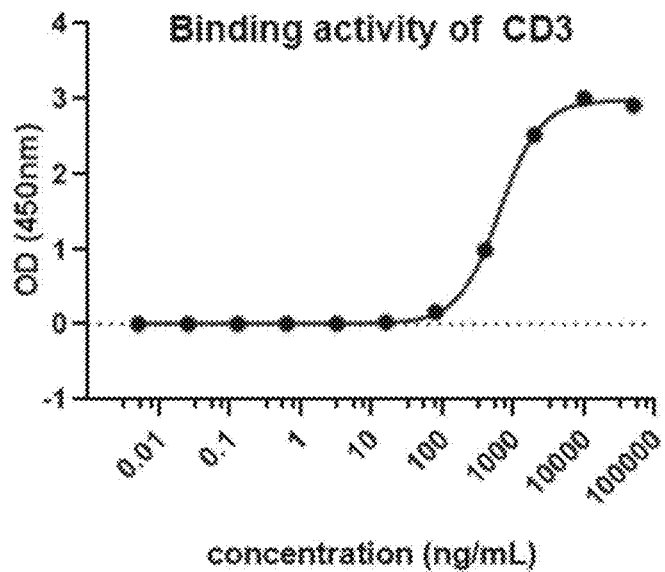
FIG. 5B shows binding of CMD016 against recombinant human CD3 as measured by ELISA.

The results indicate that CMD016 binds to human ENPP3 with $EC_{50}$ of 2.29 nM (FIG. 5A), and binds to human CD3 with $EC_{50}$ of 5.28 nM (FIG. 5B). These results suggest that CMD016 can bind to both ENPP3 and CD3 with high affinity.

Example 8. Binding of the Bispecific Antibody to Cancer Cell Lines

Figure 6A:
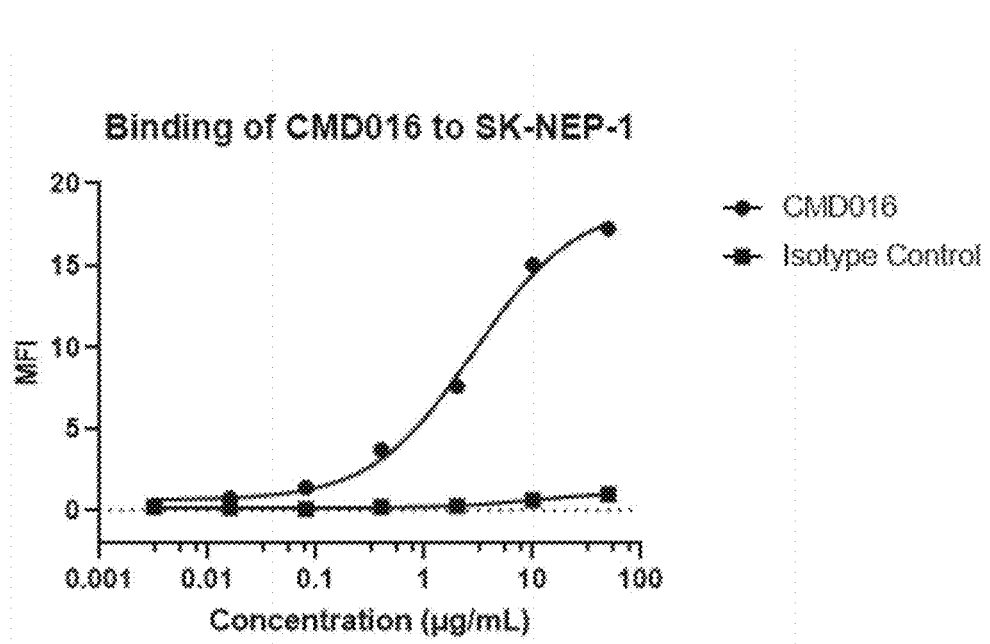
FIG. 6A shows binding of CMD016 against ENPP3 positive cancer cell line SK-Nep-1 as measured by flow cytometry. An IgG4 isotype antibody is used as negative control.
Figure 6B:
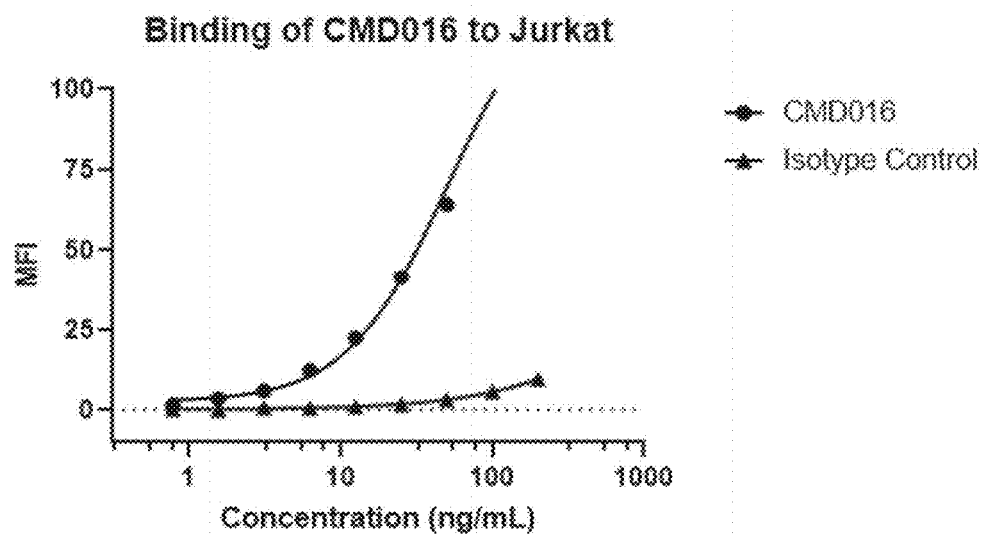
FIG. 6B shows binding of CMD016 against CD3 positive Jurkat cells as measured by flow cytometry. An IgG4 isotype antibody is used as negative control.

To determine binding affinity of the bispecific antibody CMD016 to cell surface-associated ENPP3 and CD3, flow cytometry was carried out using ENPP3 positive cancer cell line SK-Nep-1 and CD3 positive Jurkat cell line. The procedures were similar to those described in Example 4. The results were shown in FIGS. 6A-6B.

The results indicate that CMD016 binds well to SK-Nep-1 and Jurkat cells. This suggests that CMD016 can bind to both cancer cells expressing ENPP3 and cells expressing CD3.

Example 9. Bispecific Antibody Mediated Killing of Human Cancer Cell Lines

Bispecific T cell engager can simultaneously bind to a tumor antigen and a T cell antigen (e.g., CD3 molecular on T cell surface) causing aggregation and activation of T cells, eventually leading to the killing of tumor cells. To evaluate killing efficiency of the bispecific antibody CMD016, CCK8 assay was performed using tumor cell line LS174T-ENPP3 stably expressing ENPP3 as target cells. ENPP3 negative cell line LS174T was used as negative control.

$3 \times 10^4$ LS174T-ENPP3 cells were seeded in 100 μl RPMI 1640 complete medium overnight. Meanwhile, frozen PBMCs were revived and inoculated in 30 mL RPMI 1640 complete medium overnight. At the second day, $1.5 \times 10^5$ PBMCs in 50 μl RPMI 1640 complete medium were added. Then, 50 μl antibodies (5-fold serially diluted from 4 μg/ml) were added into each well. 48 h after incubation, the medium was removed and 100 μl RPMI 1640 complete medium containing 10% CCK8 was added and incubated 30 minutes in a $CO_2$ incubator. Cell killing activity was measured by using microplate reader according to the manufacturer's instructions.

Figure 7:
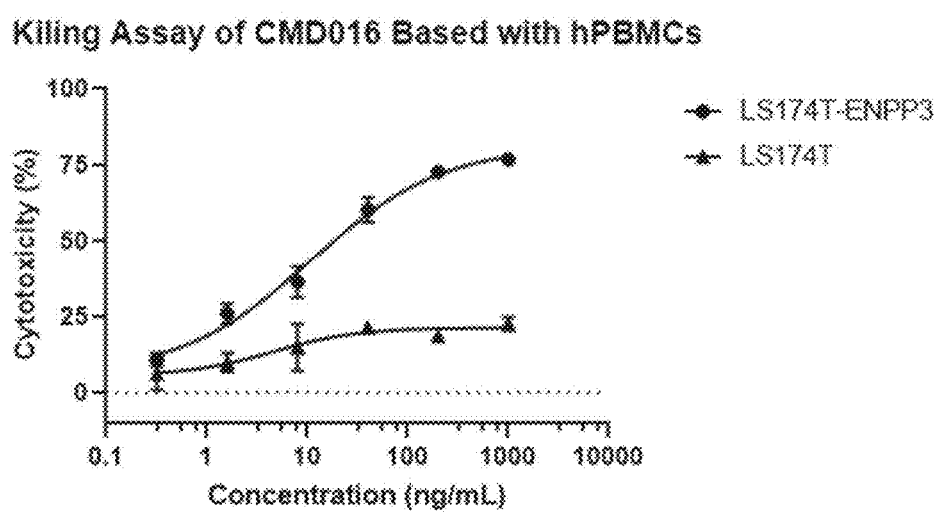
FIG. 7 shows killing of CMD016 against LS174T-ENPP3 cells stably expressing ENPP3 in the presence of human PBMCs. ENPP3 negative LS174T cell line is used as negative control.

The results were shown in FIG. 7. The results indicate that nearly 80% LS174T-ENPP3 cells were killed in the presence of CMD016 and PBMCs. The $EC_{50}$ of LS174T-ENPP3 killing by CMD016 is 10.98 ng/ml. The results have demonstrated CMD016 possesses potent killing capability against LS174T-ENPP3 cells stably expressing ENPP3, supporting its anti-tumor efficacy.

Example 10. Bispecific Antibody Mediated Inhibition of Tumor Growth in Mice

Pharmacokinetic Measurement

Three NOD/SCID mice were administered intravenously with 300 μg CMD016 on day 0. Plasma samples were collected at time points 24 hr, 48 hr, 72 hr and 96 hr after treatment and used for measurement of antibody serum concentration by ELISA.

Figure 8:
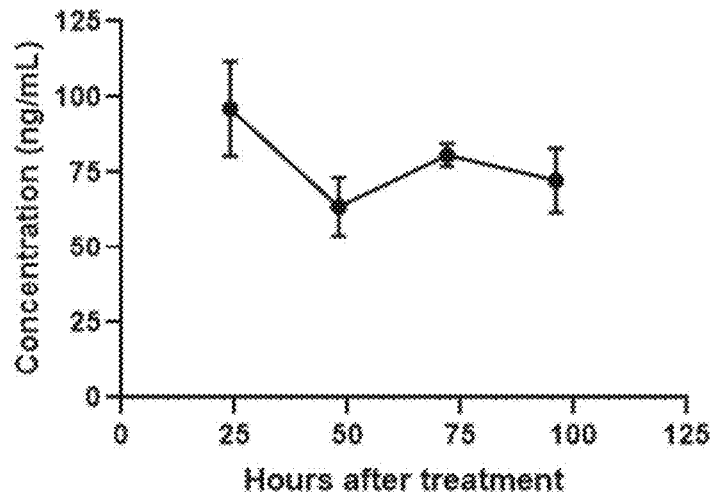
FIG. 8 shows concentration of CMD016 in serum from CMD016-treated mice at 24 hr, 48 hr, 72 hr and 96 hr after treatment.

The result indicated that the serum concentration of CMD016 was gradually decreased but still maintained a relatively high level until the end point, and the calculated serum half-life ($t_{1/2}$) was around 115.39 hours (FIG. 8).

In-Vivo Tumor Growth Inhibition $2.5 \times 10^6$ effector cells human PBMCs and $2.5 \times 10^6$ ENPP3 expressing tumor cells LS174T-ENPP3 were mixed and inoculated subcutaneously into the right side of abdomen of B-NDG mice. In experiment groups, 33.3 μg/kg (low-dose group), 100 μg/kg (medium-dose group) and 300 μg/kg (high-dose group) of CMD016 were injected intravenously into mice, respectively. These mice were dosed twice a week. The negative control group mice were dosed intravenously with PBS. Tumor volume and body weight of mice were measured at day 0, 3, 6, 10, 13 and 21 after the treatment. After three weeks of the treatment, mice were sacrificed and tumor weight was measured. Tumor growth inhibition rate was calculated by using the following formula: (Average tumor weight of control group—average tumor weight of experiment group)/average tumor weight of control group.

Figure 9A:
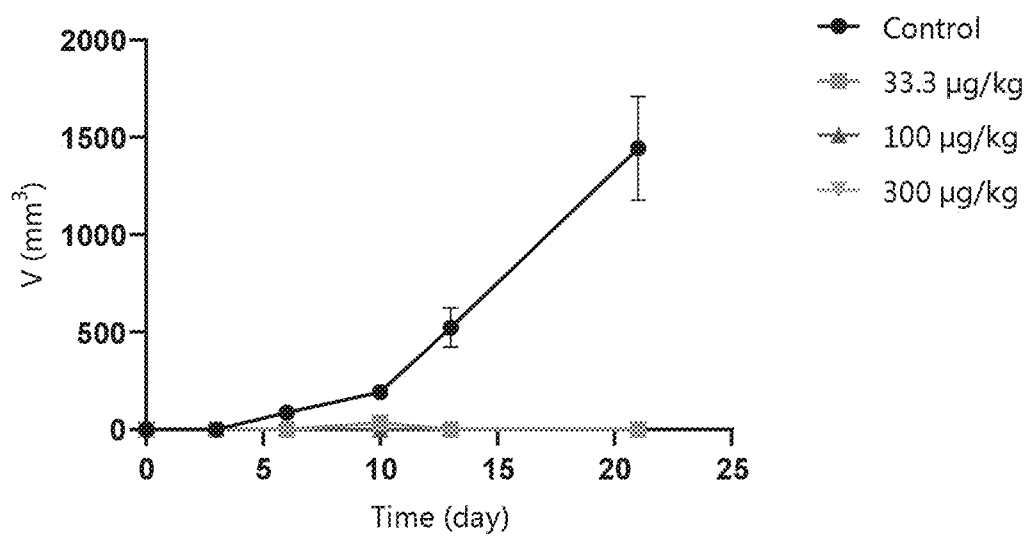
FIG. 9A shows tumor volume in mice treated with 33.3 µg/kg, 100 µg/kg and 300 µg/kg of CMD016. The mice treated with PBS are used as negative control.
Figure 9B:
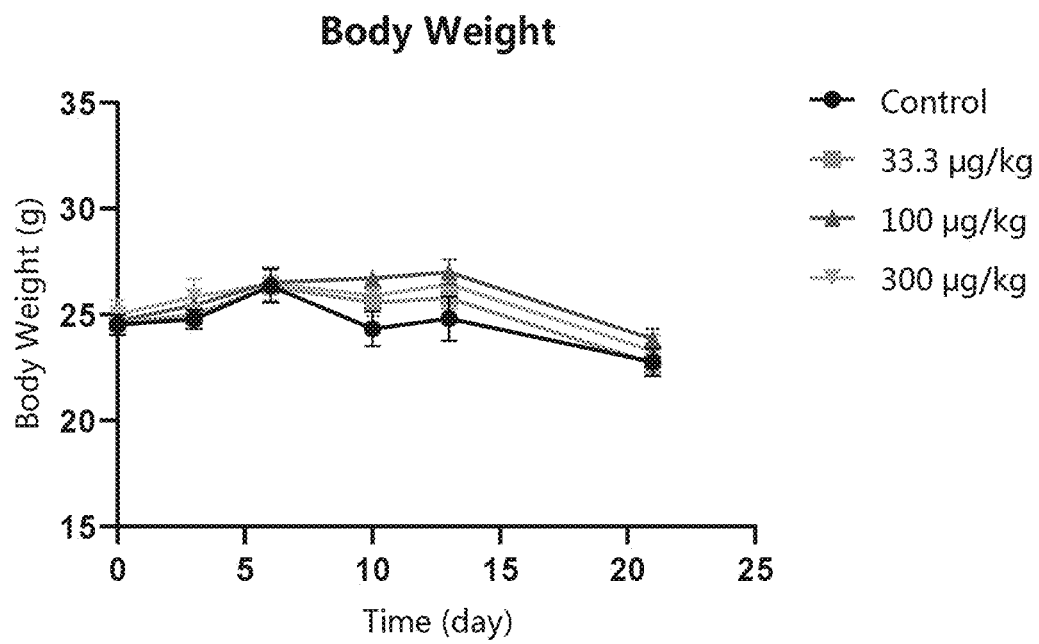
FIG. 9B shows body weight of mice treated with 33.3 µg/kg, 100 µg/kg and 300 µg/kg of CMD016. The mice treated with PBS are used as negative control.
Figure 9C:
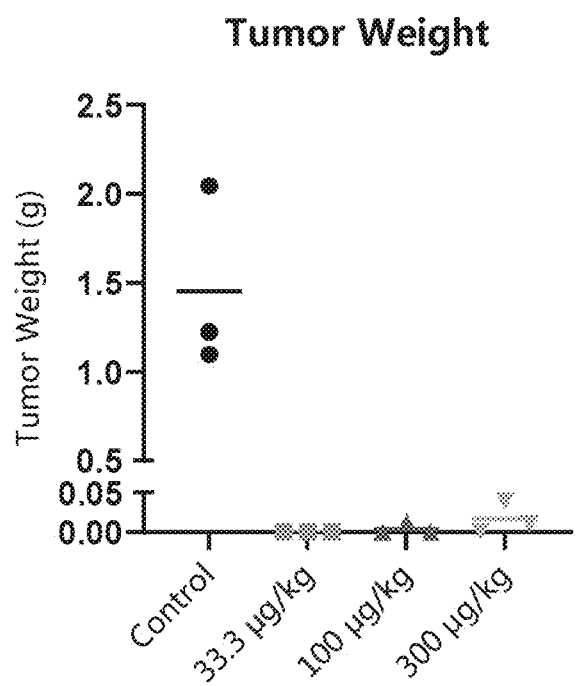
FIG. 9C shows tumor weight in mice treated with 33.3 µg/kg, 100 µg/kg and 300 µg/kg of CMD016. The mice treated with PBS are used as negative control.

The results indicate that CMD016 exhibits potent inhibition of tumor growth in all of the low-dose group, medium-dose group and high-dose group (FIG. 9A). The body weight of mice in all groups only has minor variation (FIG. 9B). All of the low-dose group, medium-dose group and high-dose group show over 95% inhibition rate of tumor growth (FIG. 9C), suggesting significant in vivo anti-tumor effect of CMD016.

In summary, the results have demonstrated that CMD016 has a long serum half-life, and can specifically and potently inhibit growth of the tumor cells expressing ENPP3, suggesting its potential for treating ENPP3 positive cancers.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

SEQUENCE LISTING

```
Sequence total quantity: 35
SEQ ID NO: 1             moltype = AA  length = 13
FEATURE                  Location/Qualifiers
REGION                   1..13
                         note = 3A10 mAb LCDR1
source                   1..13
                         mol_type = protein
                         organism = synthetic construct
SEQUENCE: 1
SGSSSNIGNN YVS                                                           13

SEQ ID NO: 2             moltype = AA  length = 7
FEATURE                  Location/Qualifiers
REGION                   1..7
                         note = 3A10 mAb LCDR2
source                   1..7
                         mol_type = protein
                         organism = synthetic construct
SEQUENCE: 2
DNNKRPS                                                                   7
```

```
SEQ ID NO: 3              moltype = AA  length = 11
FEATURE                   Location/Qualifiers
REGION                    1..11
                          note = 3A10 mAb LCDR3
source                    1..11
                          mol_type = protein
                          organism = synthetic construct
SEQUENCE: 3
GVWDSSLRAE L                                                          11

SEQ ID NO: 4              moltype = AA  length = 110
FEATURE                   Location/Qualifiers
REGION                    1..110
                          note = 3A10 mAb VL
source                    1..110
                          mol_type = protein
                          organism = synthetic construct
SEQUENCE: 4
QSVVTQPPSV SAAPGQKVTI SCSGSSSNIG NNYVSWYQQL PGTAPKLLIY DNNKRPSGIP     60
DRFSGSKSGT SATLGIDGLR TGDEAEYFCG VWDSSLRAEL FAGGTKVTVL               110

SEQ ID NO: 5              moltype = AA  length = 216
FEATURE                   Location/Qualifiers
REGION                    1..216
                          note = 3A10 mAb Light chain
source                    1..216
                          mol_type = protein
                          organism = synthetic construct
SEQUENCE: 5
QSVVTQPPSV SAAPGQKVTI SCSGSSSNIG NNYVSWYQQL PGTAPKLLIY DNNKRPSGIP     60
DRFSGSKSGT SATLGIDGLR TGDEAEYFCG VWDSSLRAEL FAGGTKVTVL SQPKAAPSVT    120
LFPPSSEELQ ANKATLVCLI SDFYPGAVTV AWKADSSPVK AGVETTTPSK QSNNKYAASS    180
YLSLTPEQWK SHKSYSCQVT HEGSTVEKTV APTECS                              216

SEQ ID NO: 6              moltype = AA  length = 5
FEATURE                   Location/Qualifiers
REGION                    1..5
                          note = 3A10 mAb HCDR1
source                    1..5
                          mol_type = protein
                          organism = synthetic construct
SEQUENCE: 6
NAWMS                                                                  5

SEQ ID NO: 7              moltype = AA  length = 17
FEATURE                   Location/Qualifiers
REGION                    1..17
                          note = 3A10 mAb HCDR2
source                    1..17
                          mol_type = protein
                          organism = synthetic construct
SEQUENCE: 7
YISSSGSTIY YADSVKG                                                    17

SEQ ID NO: 8              moltype = AA  length = 9
FEATURE                   Location/Qualifiers
REGION                    1..9
                          note = 3A10 mAb HCDR3
source                    1..9
                          mol_type = protein
                          organism = synthetic construct
SEQUENCE: 8
LAGPYYFDY                                                              9

SEQ ID NO: 9              moltype = AA  length = 118
FEATURE                   Location/Qualifiers
REGION                    1..118
                          note = 3A10 mAb VH
source                    1..118
                          mol_type = protein
                          organism = synthetic construct
SEQUENCE: 9
EVQLVESGGG LVKPGGSLRL SCAASGFTFS NAWMSWVRQA PGKGLEWVSY ISSSGSTIYY     60
ADSVKGRFTI SRDNAKNSLY LQMNSLRAED TAVYYCARLA GPYYFDYWGQ GTLVTVSS     118
```

```
SEQ ID NO: 10           moltype = AA  length = 448
FEATURE                 Location/Qualifiers
REGION                  1..448
                        note = 3A10 mAb Heavy chain
source                  1..448
                        mol_type = protein
                        organism = synthetic construct
SEQUENCE: 10
EVQLVESGGG LVKPGGSLRL SCAASGFTFS NAWMSWVRQA PGKGLEWVSY ISSSGSTIYY   60
ADSVKGRFTI SRDNAKNSLY LQMNSLRAED TAVYYCARLA GPYYFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 11           moltype = AA  length = 14
FEATURE                 Location/Qualifiers
REGION                  1..14
                        note = 3A10 HBiTE CD3 LCDR1
source                  1..14
                        mol_type = protein
                        organism = synthetic construct
SEQUENCE: 11
RSSTGAVTTS NYAN                                                    14

SEQ ID NO: 12           moltype = AA  length = 7
FEATURE                 Location/Qualifiers
REGION                  1..7
                        note = 3A10 HBiTE CD3 LCDR2
source                  1..7
                        mol_type = protein
                        organism = synthetic construct
SEQUENCE: 12
GANKRAP                                                             7

SEQ ID NO: 13           moltype = AA  length = 9
FEATURE                 Location/Qualifiers
REGION                  1..9
                        note = 3A10 HBiTE CD3 LCDR3
source                  1..9
                        mol_type = protein
                        organism = synthetic construct
SEQUENCE: 13
ALWYSNLWV                                                           9

SEQ ID NO: 14           moltype = AA  length = 110
FEATURE                 Location/Qualifiers
REGION                  1..110
                        note = 3A10 HBiTE CD3 VL
source                  1..110
                        mol_type = protein
                        organism = synthetic construct
SEQUENCE: 14
EIVVTQSPAT LSVSPGERAT LSCRSSTGAV TTSNYANWVQ QKPGQAPRGL IGGANKRAPG   60
VPARFSGSLS GDEATLTISS LQSEDFAVYY CALWYSNLWV FGQGTKLEIK             110

SEQ ID NO: 15           moltype = AA  length = 559
FEATURE                 Location/Qualifiers
REGION                  1..559
                        note = 3A10 HBiTE light chain
source                  1..559
                        mol_type = protein
                        organism = synthetic construct
SEQUENCE: 15
QSVVTQPPSV SAAPGQKVTI SCSGSSSNIG NNYVSWYQQL PGTAPKLLIY DNNKRPSGIP   60
DRFSGSKSGT SATLGIDGLR TGDEAEYFCG VWDSSLRAEL FAGGTKVTVL GSGGGGSGGG  120
GSEIVVTQSP ATLSVSPGER ATLSCRSSTG AVTTSNYANW VQQKPGQAPR GLIGGANKRA  180
PGVPARFSGS LSGDEATLTI SSLQSEDFAV YYCALWYSNL WVFGQGTKLE IKRTVAAPSV  240
FIFPPSDEQL KSGTASVVCL LNNFYPREAK VQWKVDNALQ SGNSQESVTE QDSKDSTYSL  300
SSTLTLSKAD YEKHKVYACE VTHQGLSSPV TKSFNRGECP PCPAPELLGG PSVFLFPPKP  360
KDTLMISRTP EVTCVVVDVS HEDPEVKFNW YVDGVEVHNA KTKPREEQYN STYRVVSVLT  420
VLHQDWLNGK EYKCKVSNKA LPAPIEKTIS KAKGQPREPQ VYTLPPSRDE LTKNQVSLLC  480
LVKGFYPSDI AVEWESNGQP ENNYKTTPPV LDSDGSFFLH SKLTVDKSRW QQGNVFSCSV  540
MHEALHNHYT QKSLSLSPG                                              559
```

```
SEQ ID NO: 16              moltype = AA   length = 7
FEATURE                    Location/Qualifiers
REGION                     1..7
                           note = 3A10 HBiTE CD3 HCDR1
source                     1..7
                           mol_type = protein
                           organism = synthetic construct
SEQUENCE: 16
GFTFNTY                                                                      7

SEQ ID NO: 17              moltype = AA   length = 8
FEATURE                    Location/Qualifiers
REGION                     1..8
                           note = 3A10 HBiTE CD3 HCDR2
source                     1..8
                           mol_type = protein
                           organism = synthetic construct
SEQUENCE: 17
RSKYNNYA                                                                     8

SEQ ID NO: 18              moltype = AA   length = 14
FEATURE                    Location/Qualifiers
REGION                     1..14
                           note = 3A10 HBiTE CD3 HCDR3
source                     1..14
                           mol_type = protein
                           organism = synthetic construct
SEQUENCE: 18
HGNFGSSYVS YFAY                                                             14

SEQ ID NO: 19              moltype = AA   length = 125
FEATURE                    Location/Qualifiers
REGION                     1..125
                           note = 3A10 HBiTE CD3 VH
source                     1..125
                           mol_type = protein
                           organism = synthetic construct
SEQUENCE: 19
EVQLVESGGG LVQPGGSLRL SCAASGFTFN TYAMNWVRQA PGKGLEWVAR IRSKYNNYAT           60
YYADSVKGRF TISRDDSKNT LYLQMNSLRA EDTAVYYCAR HGNFGSSYVS YFAYWGQGTT          120
VTVSS                                                                      125

SEQ ID NO: 20              moltype = AA   length = 581
FEATURE                    Location/Qualifiers
REGION                     1..581
                           note = 3A10 HBiTE heavy chain
source                     1..581
                           mol_type = protein
                           organism = synthetic construct
SEQUENCE: 20
EVQLVESGGG LVKPGGSLRL SCAASGFTFS NAWMSWVRQA PGKGLEWVSY ISSSGSTIYY           60
ADSVKGRFTI SRDNAKNSLY LQMNSLRAED TAVYYCARLA GPYYFDYWGQ GTLVTVSSGS          120
GGSGGGGSGG GGSEVQLVES GGGLVQPGGS LRLSCAASGF TFNTYAMNWV RQAPGKGLEW          180
VARIRSKYNN YATYYADSVK GRFTISRDDS KNTLYLQMNS LRAEDTAVYY CARHGNFGSS          240
YVSYFAYWGQ GTTVTVSSAS TKGPSVFPLA PSSKSTSGGT AALGCLVKDY FPEPVTVSWN          300
SGALTSGVHT FPAVLQSSGL YSLSSVVTVP SSSLGTQTYI CNVNHKPSNT KVDKKVEPKS          360
CPPCPAPELL GGPSVFLFPP KPKDTLMISR TPEVTCVVVD VSHEDPEVKF NWYVDGVEVH          420
NAKTKPREEQ YNSTYRVVSV LTVLHQDWLN GKEYKCKVSN KALPAPIEKT ISKAKGQPRE          480
PQVYTLPPSR DELTKNQVSL LCLVKGFYPS DIAVEWESNG QPENNYKTTP PVLDSDGSFF          540
LHSKLTVDKS RWQQGNVFSC SVMHEALHNH YTQKSLSLSP G                              581

SEQ ID NO: 21              moltype = AA   length = 12
FEATURE                    Location/Qualifiers
REGION                     1..12
                           note = 3A10 HBiTE light chain linker
source                     1..12
                           mol_type = protein
                           organism = synthetic construct
SEQUENCE: 21
GSGGGGSGGG GS                                                               12

SEQ ID NO: 22              moltype = AA   length = 15
FEATURE                    Location/Qualifiers
REGION                     1..15
                           note = 3A10 HBiTE heavy chain linker
source                     1..15
                           mol_type = protein
                           organism = synthetic construct
```

```
SEQUENCE: 22
GSGGSGGGGS GGGGS                                                      15

SEQ ID NO: 23           moltype = DNA  length = 68
FEATURE                 Location/Qualifiers
misc_feature            1..68
                        note = primer
source                  1..68
                        mol_type = other DNA
                        organism = synthetic construct
SEQUENCE: 23
gaatgcggcc gcaaactaca agacagactt gcaaagaag gcatgcacag ctcagcactg       60
ctctgttg                                                              68

SEQ ID NO: 24           moltype = DNA  length = 62
FEATURE                 Location/Qualifiers
misc_feature            1..62
                        note = primer
source                  1..62
                        mol_type = other DNA
                        organism = synthetic construct
SEQUENCE: 24
tcagcactgc tctgttgcct ggtcctcctg actggggtga gggccgaggt gcagctggtg     60
ga                                                                    62

SEQ ID NO: 25           moltype = DNA  length = 47
FEATURE                 Location/Qualifiers
misc_feature            1..47
                        note = primer
source                  1..47
                        mol_type = other DNA
                        organism = synthetic construct
SEQUENCE: 25
cggtgggcat gtgtgagttt tgtcacaaga tttgggctca actttct                   47

SEQ ID NO: 26           moltype = DNA  length = 64
FEATURE                 Location/Qualifiers
misc_feature            1..64
                        note = primer
source                  1..64
                        mol_type = other DNA
                        organism = synthetic construct
SEQUENCE: 26
tcagcactgc tctgttgcct ggtcctcctg actggggtga gggcccagtc tgtcgtgacg     60
cagc                                                                  64

SEQ ID NO: 27           moltype = DNA  length = 42
FEATURE                 Location/Qualifiers
misc_feature            1..42
                        note = primer
source                  1..42
                        mol_type = other DNA
                        organism = synthetic construct
SEQUENCE: 27
cgattctaga atcatgaaca ttctgtaggg gccactgtct tc                        42

SEQ ID NO: 28           moltype = DNA  length = 24
FEATURE                 Location/Qualifiers
misc_feature            1..24
                        note = primer
source                  1..24
                        mol_type = other DNA
                        organism = synthetic construct
SEQUENCE: 28
gacaaaactc acacatgccc accg                                            24

SEQ ID NO: 29           moltype = DNA  length = 38
FEATURE                 Location/Qualifiers
misc_feature            1..38
                        note = primer
source                  1..38
                        mol_type = other DNA
                        organism = synthetic construct
SEQUENCE: 29
cgattctaga atcatttacc cggggacagg gagaggct                             38
```

```
SEQ ID NO: 30            moltype = DNA  length = 68
FEATURE                  Location/Qualifiers
misc_feature             1..68
                         note = primer
source                   1..68
                         mol_type = other DNA
                         organism = synthetic construct
SEQUENCE: 30
gaatgcggcc gcaaactaca agacagactt gcaaagaag gcatgcacag ctcagcactg      60
ctctgttg                                                             68

SEQ ID NO: 31            moltype = DNA  length = 46
FEATURE                  Location/Qualifiers
misc_feature             1..46
                         note = primer
source                   1..46
                         mol_type = other DNA
                         organism = synthetic construct
SEQUENCE: 31
gccagagcca cctccgccgg atcctaggac ggtcaccttg gtccct                   46

SEQ ID NO: 32            moltype = DNA  length = 32
FEATURE                  Location/Qualifiers
misc_feature             1..32
                         note = primer
source                   1..32
                         mol_type = other DNA
                         organism = synthetic construct
SEQUENCE: 32
ggatccgggg gttcaggcgg aggtggctct gg                                  32

SEQ ID NO: 33            moltype = DNA  length = 24
FEATURE                  Location/Qualifiers
misc_feature             1..24
                         note = primer
source                   1..24
                         mol_type = other DNA
                         organism = synthetic construct
SEQUENCE: 33
ggatccggcg gaggtggctc tggc                                           24

SEQ ID NO: 34            moltype = DNA  length = 36
FEATURE                  Location/Qualifiers
misc_feature             1..36
                         note = primer
source                   1..36
                         mol_type = other DNA
                         organism = synthetic construct
SEQUENCE: 34
tgatctagaa ttaacccgga gacagggaga ggctct                              36

SEQ ID NO: 35            moltype = AA  length = 6
FEATURE                  Location/Qualifiers
source                   1..6
                         mol_type = protein
                         organism = synthetic construct
SEQUENCE: 35
HHHHHH                                                                6
```

The invention claimed is:

1. A method of treating a cancer in a human subject having the cancer, comprising administering to the human subject an effective amount of an antibody molecule that specifically binds to ENPP3 or an antigen binding fragment thereof comprising a light chain variable region (VL) and a heavy chain variable region (VH), wherein the VL comprises LCDRs 1-3 having the amino acid sequences as set forth in SEQ ID NOs: 1-3 respectively, and the VH comprises HCDRs 1-3 having the amino acid sequences as set forth in SEQ ID NOs: 6-8 respectively, and wherein the cancer is an ENPP3 positive cancer.

2. The method according to claim 1, wherein the VL comprises the amino acid sequence as set forth in SEQ ID NO: 4 or an amino acid sequence having at least 80%, at least 85%, at least 90%, at least 95%, at least 98%, or at least 99% sequence identity to SEQ ID NO: 4, and the VH comprises the amino acid sequence as set forth in SEQ ID NO: 9 or an amino acid sequence having at least 80%, at least 85%, at least 90%, at least 95%, at least 98%, or at least 99% sequence identity to SEQ ID NO: 9.

3. The method according to claim 1, wherein the antibody molecule is of an isotype selected from the group consisting of IgG, IgA, IgM, IgE and IgD.

4. The method according to claim 1, wherein the antibody molecule is of a subtype selected from the group consisting of IgG1, IgG2, IgG3, and IgG4.

5. The method according to claim 1, wherein the antigen binding fragment is selected from the group consisting of Fab, Fab', F(ab')$_2$, Fv, scFv, and ds-scFv.

6. The method according to claim 1, wherein the antibody molecule comprises a light chain comprising an amino acid sequence as set forth in SEQ ID NO: 5 or an amino acid sequence having at least 80%, at least 85%, at least 90%, at least 95%, at least 98%, or at least 99% sequence identity to SEQ ID NO: 5 and a heavy chain comprising an amino acid sequence as set forth in SEQ ID NO: 10 or an amino acid sequence having at least 80%, at least 85%, at least 90%, at least 95%, at least 98%, or at least 99% sequence identity to SEQ ID NO: 10.

7. The method according to claim 1, wherein the antibody molecule is a bispecific antibody molecule which further comprises a second antigen binding region that binds to a second antigen, wherein the second antigen is a tumor associated antigen, an immune cell antigen, or a T-cell antigen.

8. The method according to claim 7, wherein the T-cell antigen is selected from the group consisting of T cell receptor (TCR), CD3, CD4, CD8, CD16, CD25, CD28, CD38, CD44, CD62L, CD69, ICOS, 41-BB (CD137), and NKG2D.

9. The method according to claim 7, wherein the second antigen is CD3, and the second antigen binding region comprises a VL comprising the amino acid sequence as set forth in SEQ ID NO: 14 and a VH comprising the amino acid sequence as set forth in SEQ ID NO: 19.

10. The method according to claim 9, wherein the VL of the second antigen binding region is linked to the C-terminus of the VL of the antibody molecule that specifically binds to ENPP3, optionally via a first linker, and the VH of the second antigen binding region is linked to the C-terminus of the VH of the antibody molecule that specifically binds to ENPP3, optionally via a second linker, wherein the first linker and the second linker are the same or different.

11. The method according to claim 10, wherein the first linker comprises the amino acid sequence as set forth in SEQ ID NO: 21, and the second linker comprises the amino acid sequence as set forth in SEQ ID NO: 22.

12. The method according to claim 9, wherein the bispecific antibody molecule comprises a light chain comprising the amino acid sequence as set forth in SEQ ID NO: 15 or an amino acid sequence having at least 80%, at least 85%, at least 90%, at least 95%, at least 98%, or at least 99% sequence identity to SEQ ID NO: 15 and a heavy chain comprising the amino acid sequence as set forth in SEQ ID NO: 20 or an amino acid sequence having at least 80%, at least 85%, at least 90%, at least 95%, at least 98%, or at least 99% sequence identity to SEQ ID NO: 20.

13. The method according to claim 7, wherein the bispecific antibody molecule is a bispecific T-cell engager.

14. The method according to claim 1, wherein the cancer is selected from the group consisting of mastocytosis, leukemia, kidney cancer, lung cancer, gastric cancer, ovarian cancer, breast cancer, pancreatic cancer, colon cancer, colorectal cancer, bile duct cancer, liver cancer, and Wilms tumor.

15. The method according to claim 1, further comprising administering to the human subject a second therapeutic agent.

16. The method according to claim 15, wherein the second therapeutic agent is selected from an antibody, a chemotherapeutic agent and a small molecule drug.

17. The method according to claim 15, wherein the second therapeutic agent is selected from a Bruton's tyrosine kinase (BTK) inhibitor, a PI3K inhibitor, a HDAC inhibitor, an ERK inhibitor, a MAPK inhibitor, a PD-1/PD-L1 inhibitor, a LAG3 inhibitor, a CTLA-4 inhibitor, a TIGIT inhibitor, a TIM3 inhibitor, and glucocorticoid.

18. The method according to claim 1, wherein the VL comprises the amino acid sequence as set forth in SEQ ID NO: 4, and the VH comprises the amino acid sequence as set forth in SEQ ID NO: 9.

19. The method according to claim 1, wherein the antibody molecule comprises a light chain comprising the amino acid sequence as set forth in as set forth in SEQ ID NO: 5 and a heavy chain comprising the amino acid sequence as set forth in as set forth in SEQ ID NO: 10.

20. The method according to claim 9, wherein the bispecific antibody molecule comprises a light chain comprising the amino acid sequence as set forth in as set forth in SEQ ID NO: 15 and a heavy chain comprising the amino acid sequence as set forth in as set forth in SEQ ID NO: 20.

\* \* \* \* \*